United States Patent
Pizzi et al.

(12)

(10) Patent No.: US 10,687,749 B2
(45) Date of Patent: Jun. 23, 2020

(54) MEDICAL DEVICE FOR THE PREPARATION OF A CONCENTRATE OF CELLS

(71) Applicant: ELTEK S.p.A., Casale Monferrato (Alessandria) (IT)

(72) Inventors: Marco Pizzi, Casale Monferrato (IT); Massimo Zanin, Casale Monferrato (IT); Enrica Mortara, Casale Monferrato (IT); Chadée Chappoz, Casale Monferrato (IT); Laura Mazzucco, Casale Monferrato (IT)

(73) Assignee: ELTEK S.p.A., Casale Monferrato (Alessandria) (IT)

( * ) Notice: Subject to any disclaimer, the term of this patent is extended or adjusted under 35 U.S.C. 154(b) by 212 days.

(21) Appl. No.: 15/522,100

(22) PCT Filed: Oct. 29, 2015

(86) PCT No.: PCT/IB2015/058361
§ 371 (c)(1),
(2) Date: Apr. 26, 2017

(87) PCT Pub. No.: WO2016/067246
PCT Pub. Date: May 6, 2016

(65) Prior Publication Data
US 2017/0319118 A1    Nov. 9, 2017

(30) Foreign Application Priority Data
Oct. 31, 2014    (IT) .............................. TO2014A0897

(51) Int. Cl.
*A61B 5/15*    (2006.01)
*A61M 39/22*    (2006.01)
(Continued)

(52) U.S. Cl.
CPC .......... *A61B 5/15003* (2013.01); *A61B 5/153* (2013.01); *A61B 5/15074* (2013.01);
(Continued)

(58) Field of Classification Search
CPC .......... A61B 5/15003; A61B 5/150221; A61B 5/150236; A61B 5/150244;
(Continued)

(56) References Cited

U.S. PATENT DOCUMENTS

| | | | |
|---|---|---|---|
| 4,900,322 A * | 2/1990 | Adams | ................ A61M 1/0209 604/248 |
| 5,318,782 A | 6/1994 | Weis-Fogh | |
| 2004/0065626 A1 | 4/2004 | Woo | |

FOREIGN PATENT DOCUMENTS

| | | |
|---|---|---|
| KR | 2011-0120729 | 11/2011 |
| WO | WO 2014/093845 | 6/2014 |
| WO | WO 2015/071852 | 5/2015 |

OTHER PUBLICATIONS

International Search Report for PCT/IB2015/058361, dated Jan. 25, 2016, 16 pages.
Written Opinion of the ISA for PCT/IB2015/058361, dated Jan. 25, 2016, 6 pages.

* cited by examiner

*Primary Examiner* — Dirk R Bass
(74) *Attorney, Agent, or Firm* — Nixon & Vanderhye P.C.

(57) ABSTRACT

A medical device for the separation of a concentrate enriched with cells from a biological fluid, in particular a concentrate of stromal or stem cells from medullar aspirate or venous blood, comprises:

- a treatment container for receiving and treating the biological fluid for the purposes of its separation into a number of fractions;
- a first collection container, for receiving a first fraction of the fluid, in particular a fraction poor in said cells;
- a second collection container, for receiving a second concentrated fraction of the fluid enriched with said cells;
- a deviator valve having a first way connected or prearranged for connection to the treatment container, a second way connected or prearranged for connection to the first collection container, and a third way connected or prearranged for connection to the second collection container;
- a first line for connection of the treatment container to the first way of the deviator valve, a second line for connection of the first collection container to the second way of the deviator valve, and a third line for connection of the second collection container with the third way of the deviator valve.

The treatment container is a syringe container with a plunger having a plunger stem associated in a releasable way to a corresponding plunger head, and the first connection line comprises a first transparent tube, in particular a flexible transparent tube, and at least one of the second and third connection lines preferably comprises a second flexible tube. At least one connection line, or each connection line, further comprises:

- at least one respective hydraulic connector, for separable connection of a corresponding tube to the corresponding container and/or to the corresponding way of the deviator valve; and
- at least one automatic-closing or one-way valve.

16 Claims, 15 Drawing Sheets

(51) Int. Cl.
  *A61B 5/153* (2006.01)
  *A61M 1/02* (2006.01)
  *A61M 39/24* (2006.01)

(52) U.S. Cl.
  CPC .. *A61B 5/150221* (2013.01); *A61B 5/150236* (2013.01); *A61B 5/150244* (2013.01); *A61B 5/150366* (2013.01); *A61B 5/150389* (2013.01); *A61B 5/150503* (2013.01); *A61B 5/150755* (2013.01); *A61M 1/029* (2013.01); *A61M 39/223* (2013.01); *A61M 39/24* (2013.01); *A61M 2039/242* (2013.01); *A61M 2202/0437* (2013.01)

(58) Field of Classification Search
  CPC ........ A61B 5/150366; A61B 5/150389; A61B 5/150503; A61B 5/15074; A61B 5/150755; A61B 5/153; A61M 1/029; A61M 2039/242; A61M 2202/0437; A61M 39/223; A61M 39/24
  See application file for complete search history.

MEDICAL DEVICE FOR THE PREPARATION OF A CONCENTRATE OF CELLS

This application is the U.S. national phase of International Application No. PCT/IB2015/058361 filed Oct. 29, 2015 which designated the U.S. and claims priority to IT Patent Application No. TO2014A000897 filed Oct. 31, 2014, the entire contents of each of which are hereby incorporated by reference.

FIELD OF THE INVENTION

The present invention relates in general to medical devices and has been developed with particular reference to devices that can be used for taking a sample of a biological fluid from a subject, preferably medullar or venous blood, separating it into fractions, and obtaining a concentrate of cells from one of the separated fractions, preferably stromal or stem cells.

PRIOR ART

Recent studies have shown that the stromal component of bone marrow, constituted by a heterogeneous cell population (endothelial cells, fibroblasts, adipocytes, osteoblasts, etc.) contains non-haemopoietic stem cells having a capacity for self-maintenance and differentiation. Stromal cells, in particular conditions of culture and stimulation, have a capacity for self-maintenance and differentiation into bony tissue, cartilaginous tissue, muscular tissue, tendineous tissue, and adipose tissue. Stromal cells in culture, generally referred to as mesenchymal stem cells (MSCs), represent a population of multipotent cells that is found in bone marrow, in fatty tissue and, to a minimal extent, in peripheral blood.

Following upon centrifugation of blood, such as medullary blood, the majority of mesenchymal stem cells are to be found in a separation layer or fraction, known as buffy coat, which represents a rich source of cells and proteins that can contribute to optimizing the conditions for healing. The aforesaid fraction rich in stromal or stem cells is not only able to accelerate migration of stem cells for the repair site, but also stimulates their proliferation in the micro-environment. Typically the buffy coat appears as a yellowish-pink layer that is the thicker the higher the number of leukocytes present.

The relative ease of isolation, the high potential for expansion in vitro, and the potential of differentiation have enabled mesenchymal stem cells to be used for applications of cell therapy in the field of reparative and regenerative medicine, of aesthetic medicine, and of plastic surgery.

The procedures currently used for the preparation of concentrates of stromal cells starting from medullary aspirate are based upon devices that are generally costly and are not easy to use.

For instance, a system for sampling and separation of medullary aspirate is known from the document No. WO 2010/138895 A, on which the preamble of Claim 1 is based.

The solution envisages that the medullary aspirate taken from the patient is introduced into a centrifugable container, housed in which is a rigid insert having a density such that, following upon appropriate centrifugation of the container, different fractions of the medullary blood stratify in different positions with respect to the insert. In particular, after centrifugation, the less dense fraction of the medullary blood, i.e., the plasma, is to be found above the insert, the denser fraction, i.e., the red blood cells, underneath the insert, and the portion with intermediate density, i.e., the buffy coat, in a central funnel-shaped area of the insert itself.

The separation system then includes two syringes, which are connected to the centrifugable container by way of a cannula system and a valve device. The cannula system has two hollow elements, which can turn with respect to one another and are provided with holes at different heights to enable selective sampling of the stratified fractions within the centrifugable container. In particular, when certain upper and lower holes of the cannula system are aligned, it is possible to sample the less dense fraction (plasma) using one syringe and the fraction with intermediate density (buffy coat) using the other syringe. For this purpose, the valve device can be switched between two positions, in which the cannula system is in fluid communication with one or the other syringe.

In the device according to the document cited above, the specific construction of the centrifugable container is relatively complicated and costly, and the use of the device as a whole is inconvenient, in particular as regards operation of the cannula system and sampling of the fractions of the separated medullary blood.

SUMMARY AND AIM OF THE INVENTION

In view of what has been set forth above, the aim of the present invention is basically to provide a device of the type referred to, for separation or enrichment of a concentrate of cells starting from a biological fluid, which is simple and economically advantageous to produce, as well as being reliable, safe, precise, and convenient to use by operators.

An auxiliary object of the present invention is to provide a system comprising a device of the aforesaid type in which at least sampling of separated fractions of a biological fluid, such as blood or medullary aspirate, can be performed in an automated and hence intrinsically precise way.

The above and other aims still, which will emerge more clearly hereinafter, are achieved according to the present invention by a separation device and a separation system having the characteristics specified in the annexed claims.

BRIEF DESCRIPTION OF THE DRAWINGS

Further purposes, characteristics, and advantages of the invention will emerge from the ensuing description, with reference to the annexed drawings, which are provided purely by way of non-limiting example and in which.

DESCRIPTION OF PREFERRED EMBODIMENTS OF THE INVENTION

Reference to "an embodiment" or "one embodiment" in the framework of the present description is intended to indicate that a particular configuration, structure, or characteristic described in relation to the embodiment is comprised in at least one embodiment. Hence, phrases such as "in an embodiment" or "in one embodiment" and the like that may be present in various points of the present description do not necessarily refer to one and the same embodiment. Furthermore, particular conformations, structures, or characteristics defined in the course of the present description may be combined in any adequate way in one or more embodiments, even in ways different from the ones represented. The reference numbers and spatial references (such as "upper", "lower", "top", "bottom", "up", "down", etc.) are used herein merely for convenience and hence do not define the sphere of protection or the scope of the embodiments. In the figures, the same reference numbers are used to designate elements that are similar or technically equivalent to one another.

Figure 1:
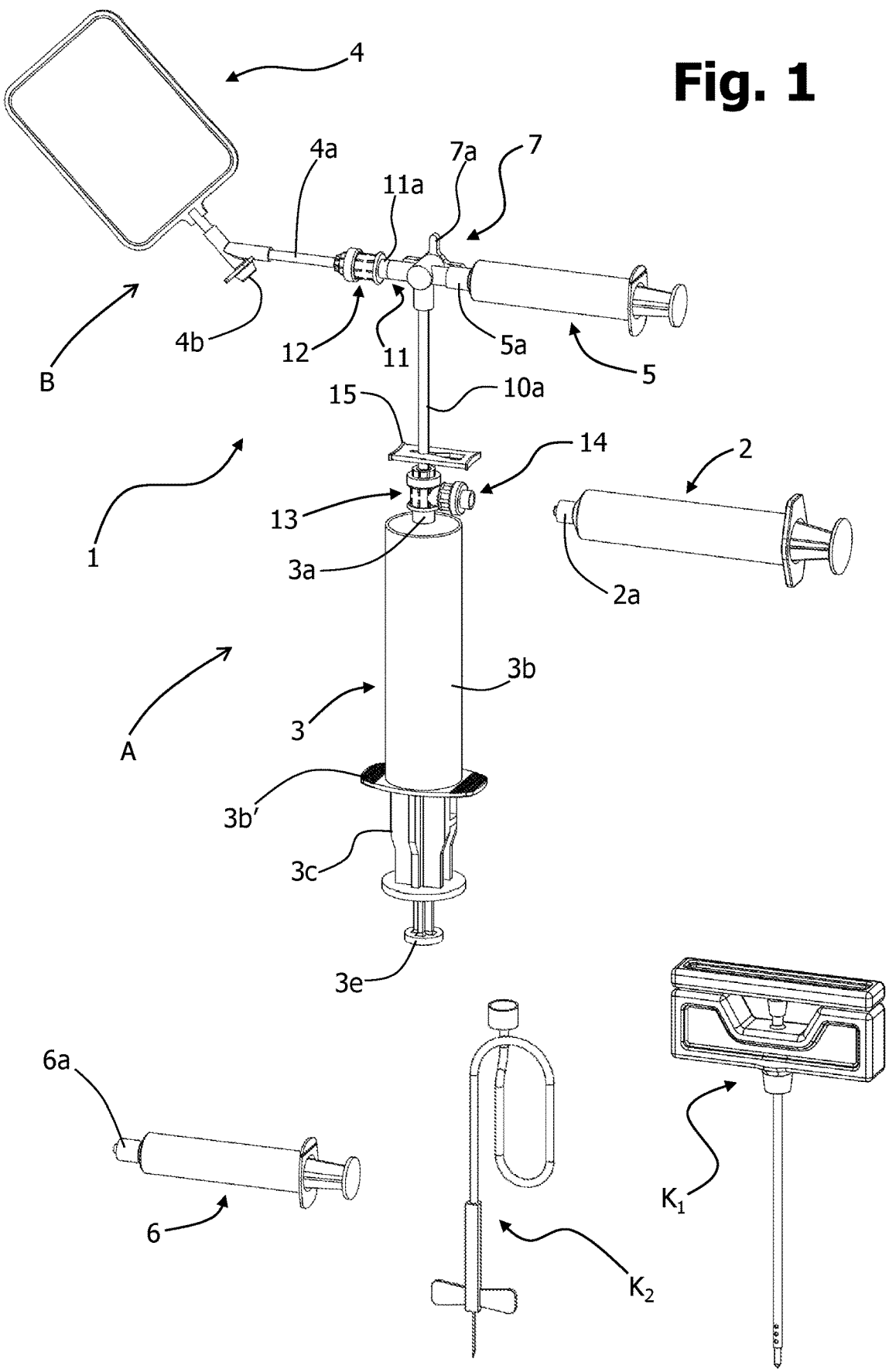
FIG. 1 is an exploded schematic view of a medical device according to an embodiment of the invention.

A possible embodiment of a medical device for separation or enrichment of a concentrate of cells starting from a biological fluid is exemplified schematically in FIG. 1, the device being designated as a whole by 1. In what follows it will be assumed that the fluid to be sampled and separated into fractions is blood, preferably medullar blood, and that the device 1 is used for the purposes of preparation of a concentrate of stromal or stem cells, i.e., the buffy coat of the separated blood, for example for regenerative applications and/or applications of physiological renewal and/or repair of tissues in specialist clinical contexts.

The device according to the invention preferentially comprises disposable components provided in sterile package. Very preferably the device comprises all the components necessary for taking a sample of medullar blood from a patient and preventing coagulation thereof, separating the sample into its fractions, and obtaining a concentrated or enriched fraction. In more general terms, the device enables treatment of a fluid in a closed system, i.e., in conditions such as to prevent any contamination of the fluid itself from outside during the various operating steps.

In the example illustrated, the device 1 comprises at least one container 2 for collecting the fluid that is to be treated, for example blood or medullary aspirate, a treatment container 3, in particular for centrifugation of blood or medullary aspirate, a container 4 for receiving a first fraction of the fluid, and a container 5 for receiving a second fraction of the fluid.

In a preferred embodiment, the device 1 includes a container 6 for the addition of an anticoagulant and at least one device for blood sampling. In the example represented, the container 6 comprises a syringe, whereas the sampling device may be of various types. FIG. 1 illustrates for this purpose two alternative versions of sampling devices $K_1$ and $K_2$ of a type in themselves known. The device $K_1$ is a device for medullary biopsy, for example including a biopsy needle and a Jamshidi needle provided with mandrel, whereas the device $K_2$ comprises a needle for venous sampling with associated a corresponding tube for connection to the container 2. In other embodiments, the device $K_2$ for sampling venous blood may consist of a simple hypodermic needle, which can be directly associated to the container 2, as described hereinafter. The container 6 and/or the device $K_1$ or $K_2$ do not necessarily form part of the device 1, and are preferably not pre-assembled on other parts described herein.

The containers 2, 3, 5, and 6 each have an attachment, preferably of a Luer type, defining a port for fluid inlet and/or outlet: these attachments are designated, respectively, by 2a, 3a, 5a, and 6a. Associated, instead, to the container 4 is a flexible tube 4a, for example moulded with the container itself, preferentially provided along which is at least one attachment and/or a valve means, described hereinafter.

In the preferred embodiment, the containers 2, 3, 5 and 6 are constituted by variable-volume containers, preferably syringes, each comprising a barrel defining the corresponding attachment and a plunger displaceable in the barrel. Very preferably, the plunger of the syringe 3 is made up of two parts that can be separated from one another, and specifically a plunger head and a plunger stem.

The container 4 is preferentially a generally pliable and/or compressible container, in particular a bag container, for example with a capacity of 30 ml, made, for example, of polymeric plastic material, such as PP, PE, PET, or an elastomer. Preferentially, associated to the tube 4a of the container 4 is a connector, for example a Y-connector provided with an area 4b that can be perforated with a needle, such as an elastomeric membrane.

The various syringes of the device 1 can be coupled in a releasable way to a hydraulic connection line, preferentially comprising one or more transparent flexible tubes, for example made of PVC, polyurethane, or some other elastomer. Preferentially, operative on said connection line are valve means, in particular selected between shut-off means and flow-deviator means, which operate or are operable to enable and/or prevent, and/or deviate a flow of fluid through certain branches of the line itself, as will emerge hereinafter. The valve means comprise a deviator valve, designated by 7, preferably of a mechanical type, namely with a control element that can be operated manually and/or mechanically, preferably without any electrical connection. La valve 7 has three ways for connection to the treatment container 3, to the first collection container 4 and to the second collection container 5, respectively. In the embodiment exemplified, this valve is constituted by a three-way tap, with corresponding knob or control element 7a, preferably comprising radial reliefs or lobes.

Preferentially, the valve means further comprise one or more automatically operated valves, including automatic- or self-closing valves, which may be at least in part integrated in corresponding separable attachments or hydraulic connectors, or else arranged in the proximity of these attachments or connectors.

The aforesaid connection line includes a first branch of line, preferentially comprising a transparent flexible tube 10a, with a first end that can be associated to the attachment 3a of the syringe 3 and a second end that can be associated to one of the ways of the valve 7. A second branch of line, which also preferentially comprises a flexible tube, is represented by the tube 4a that sets a second way of the valve 7 in fluid communication with the container 4. To the third way of the valve 7, instead, the attachment 5a of the syringe 5 can be connected directly or with interposition of a respective tube. As it can be noticed, the branch of line represented by the tube 4a is designed for fluidic connection of the container 4 only, i.e., it has no active intermediate bifurcations.

The device 1 preferentially has a modular structure, i.e., it comprises a plurality of parts or modules that are separably connected together to enable removal thereof according to the operating step of use of the device 1. Preferably, the device 1 envisages an initial configuration in which all the modules provided are associated to one another and sterilized, in particular to define a device in which the inside of all the components—such as the containers, as well as the corresponding connection lines and the valve means—are sterile and protected from any contamination from outside, enabling maintenance of a condition of sterility of the blood and of its separated or concentrated fractions, during the various operating steps of use of the device 1. As has been mentioned, the container 6 and the sampling device $K_1$ or $K_2$ are not necessarily pre-assembled on the other parts of the device 1.

In the example, the aforesaid modules include a first module A, which comprises the syringe 3 and the corresponding portion of line 10a, and a second module B, which comprises the container 4 and the corresponding portion of line 4a. The syringe 5 can in turn be considered as a third module of the device 1 in so far as it can be coupled to the connection line via the corresponding third way of the valve 7. The valve 7 may belong to any one of the modules, but preferentially it belongs to the module A, which includes the syringe 3.

Preferentially, provided at the interface between the modules of the device 1 are hydraulic connectors, preferably comprising at least two parts, which can be mechanically coupled to one another in a fluid-tight way and are designed to provide both a hydraulic connection between the modules, enabling passage of the fluid, and a mechanical connection between the modules, for the purposes of a convenient handling of the device 1. The connectors are preferably of the separable or releasable type, in particular to enable convenient separation of the modules in question, for example screw or threaded connectors, or connectors of some other quick-release type. With reference to the example represented, designated by 11 is one such releasable connector, operatively set between the modules A and B.

In a preferred embodiment, at least one automatically operated valve 12 is provided, configured to enable a one-way flow from the valve 7 along the branch 4a, and then close automatically the passage towards the valve 7 so as to prevent any contamination from outside in the case of separation of the two parts of the connector 11 (one of these parts—designated by 1a—hence providing the attachment for the container 4). As will be seen, one such valve may be integrated in a part of the connector 11, on the branch 4a downstream of the valve 7. In an embodiment such as the one exemplified, the deviator valve 7 belongs to the module A, whereas the valve 12 belongs to the module B.

In the embodiment illustrated, the attachment 3a of the syringe 3 may be associated to a connector 13, to which an end of the tube 10a is connected. The connector 13 is here a connector with a number of attachments, in particular a T-connector so as to define a connection attachment 14 for attachment 2a of the syringe 2, as will emerge more clearly hereinafter. Preferentially, provided within the connector 13 is an automatically operated valve, to enable a flow from the attachment 13 to the branch of line 10a and prevent, on the other hand, any reflux in the opposite direction. The above automatically operated valve is not shown in FIG. 1 in so far as it is integrated in the attachment 14. The automatically operated valve or valves envisaged by the device 1 may be advantageously configured as one-way or non-return valves.

One or more modules of the structure of the device 1 may also comprise at least one further shut-off member on at least one branch of a corresponding connection line, such as, for example, one or more clamp valves, one of which is designated by 15 and for simplicity will be referred to hereinafter as "clamp" and is set on the tube 10a downstream of the connector 13.

As has been mentioned, in one embodiment, at least one automatically operated valve of the device 1 is integrated at least in part in a hydraulic connector or attachment. Preferentially, one such automatically operated valve comprises an open/close element and a resilient element, such as a spring, preferably a spiral spring. The resilient element that brings about automatic closing of the open/close element preferably has a predefined or calibrated force, for example to prevent movement of the open/close element in the presence of values of pressure different from the predefined ones (such as a valve that does not open with values of negative pressure on one side of the open/close element and/or of a pressure on the opposite side higher than a predefined value). The automatically operated valve performs the function of shutting off automatically any flow during certain steps of use of the device 1 or of automatically closing a respective stretch of connection line, in particular to prevent any leakage of fluid and/or contamination from outside.

Figure 2:
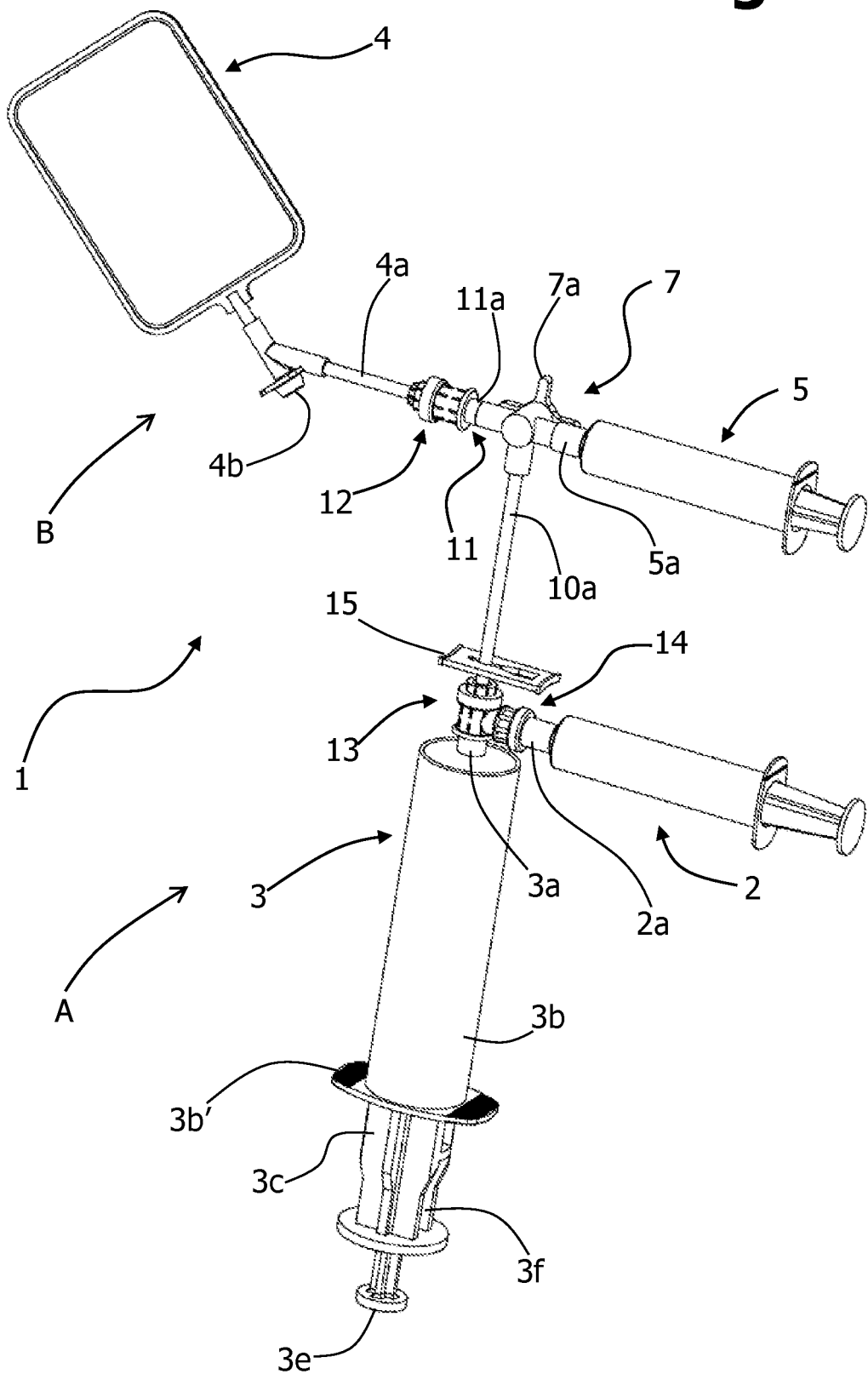
FIG. 2 is a schematic perspective view of some parts of the device of FIG. 1 in the assembled condition.
Figure 3:
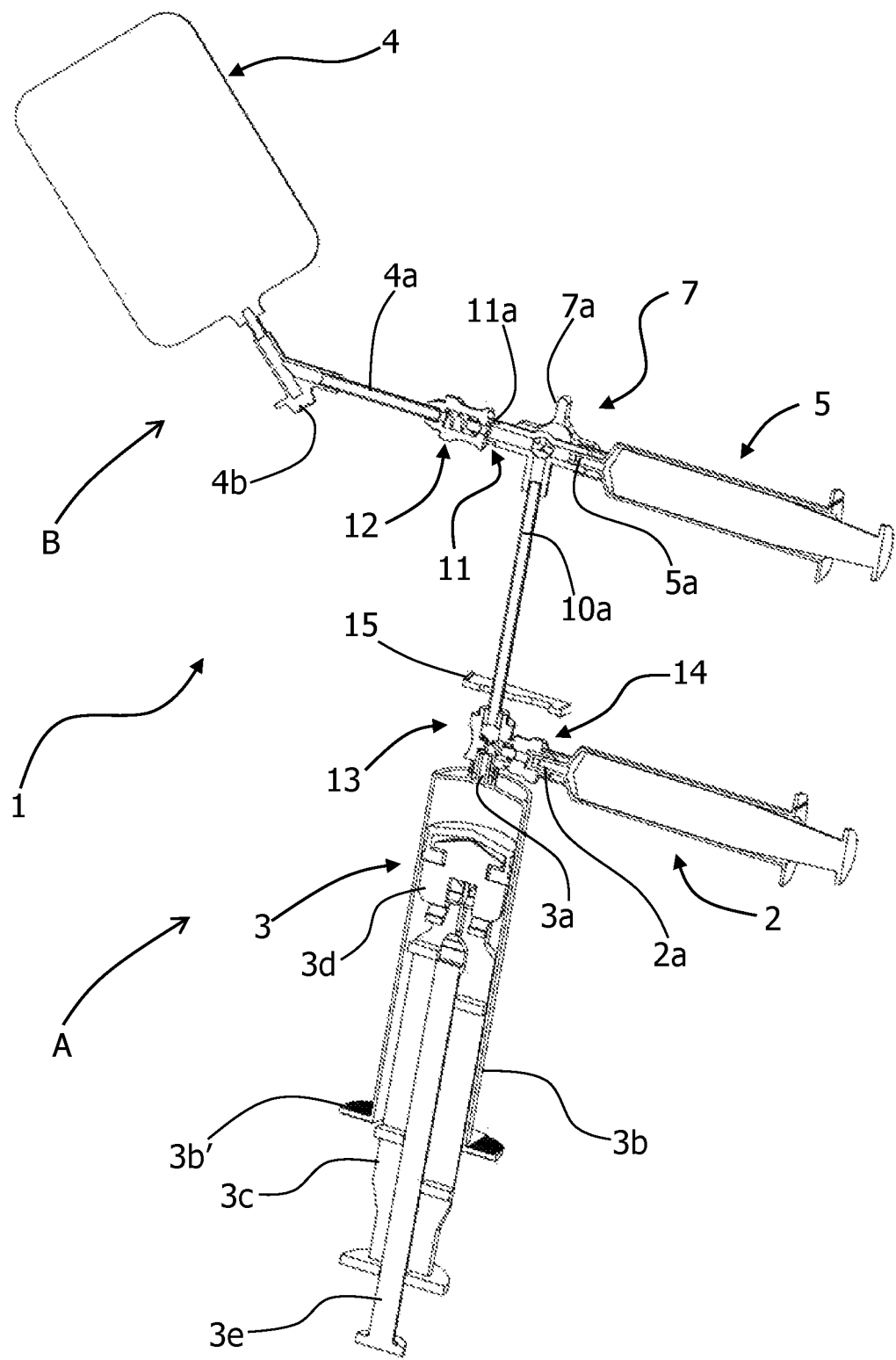
FIG. 3 is a view similar to that of FIG. 2, with the components of the device represented in cross section.

In FIG. 2 the device 1 is represented in a condition where the attachment 2a of the syringe 2 is coupled to the attachment 14, which is preferentially an attachment of a Luer type. FIG. 3 illustrates the same condition of the device 1, with the various components represented in cross section.

Figure 4:
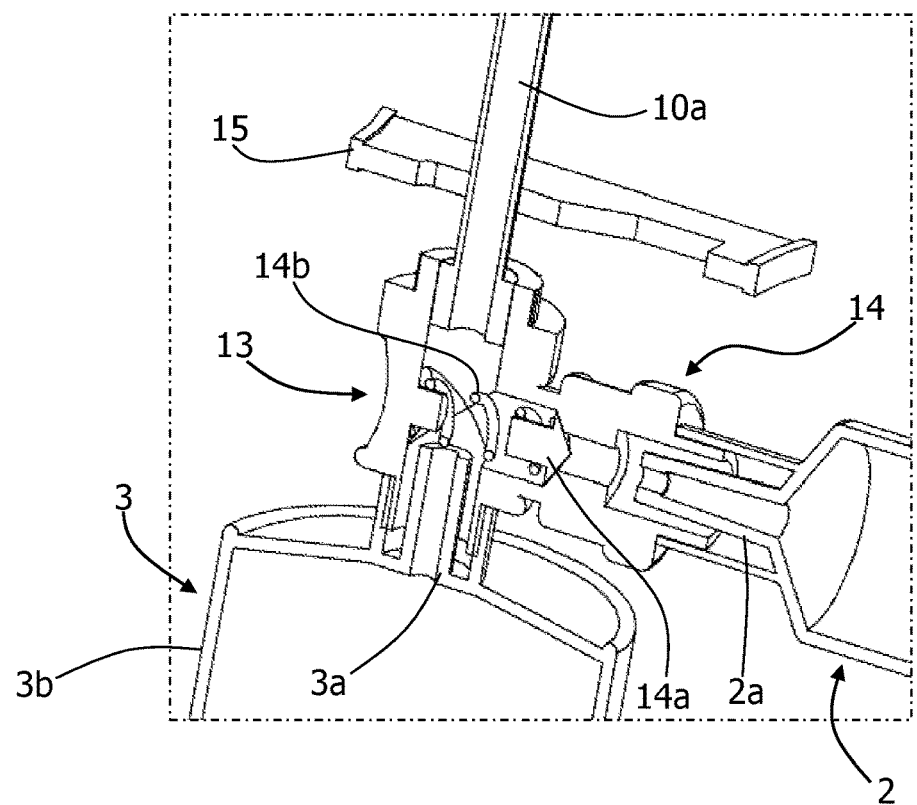
FIGS. 4 and 5 are details at an enlarged scale of FIG. 3.

FIG. 4 is a detail of FIG. 3, which shows a possible embodiment of the connector 13, set between the tube 10a and the attachment 3a of the syringe 3, where the lateral or derivation way of the connector forms the attachment 14. As has been mentioned previously, in a preferred embodiment, the attachment 13 or the connector 14 integrates or has associated an automatically operated valve. In the example represented, present within the body of the attachment 14 (or of the connector 13) is an open/close element 14a, which is urged elastically so as to close the way internal to the attachment 14, for example via a spring 14b or some other elastic element. In the presence of a flow with suitable pressure coming from the attachment 14, the open/close element 14a can recede, overcoming the elastic reaction of the spring 14b. On the other hand, in the absence of a flow from the attachment 14, the spring 14b keeps the open/close element 14a in the position where it closes the way internal to the attachment 14. Preferentially, the force of the spring 14b, the weight of the open/close element 14a, and their arrangement are predefined in such a way as to keep the open/close element 14a in a closing position also during the steps of centrifugation of the container 3 (in other words, hence, the force of the spring is such as to overcome the force exerted by the weight of the open/close element during centrifugation). Preferentially, the elements of the valve 14 are arranged along an axis that is substantially orthogonal or transverse to the axis of the container 3, and the latter, in the centrifugation steps, is set in a centrifuge in such a way that its axis is substantially in the direction of the centrifugal force.

Preferably, the open/close system 14a-14b is shaped in a way such that, in the presence of a flow from the attachment 3a of the syringe 3 towards the tube 10a, the pressure of the fluid will contribute to keep the system itself in its closing position, illustrated in FIG. 4.

Figure 5:
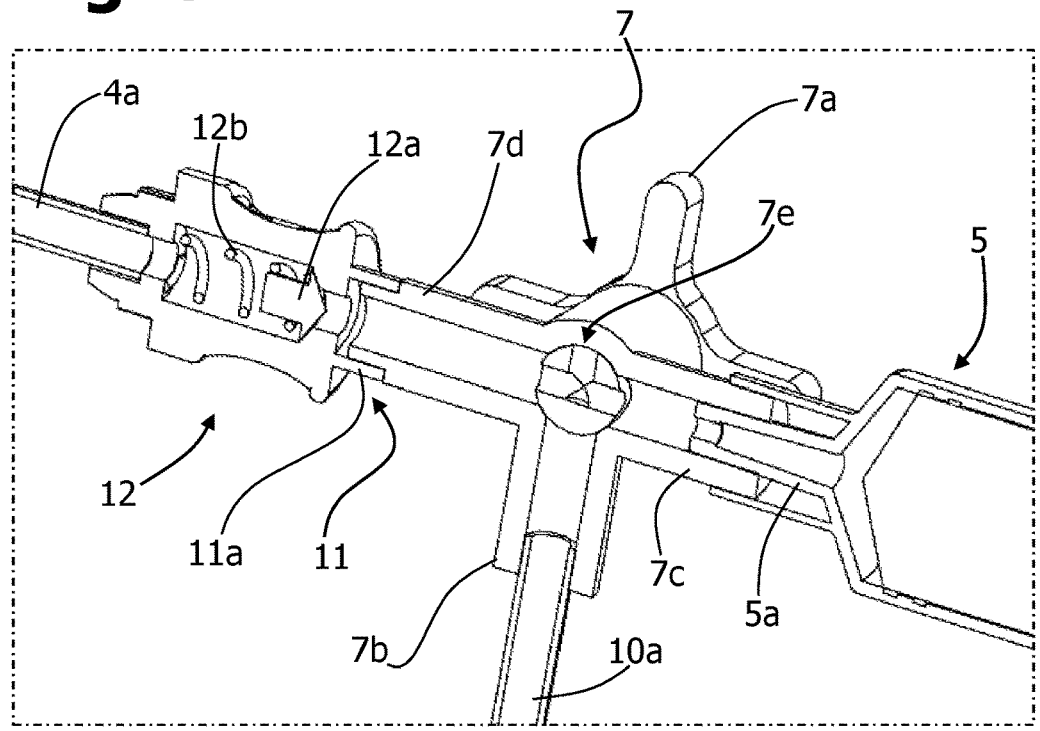
Figure 6:
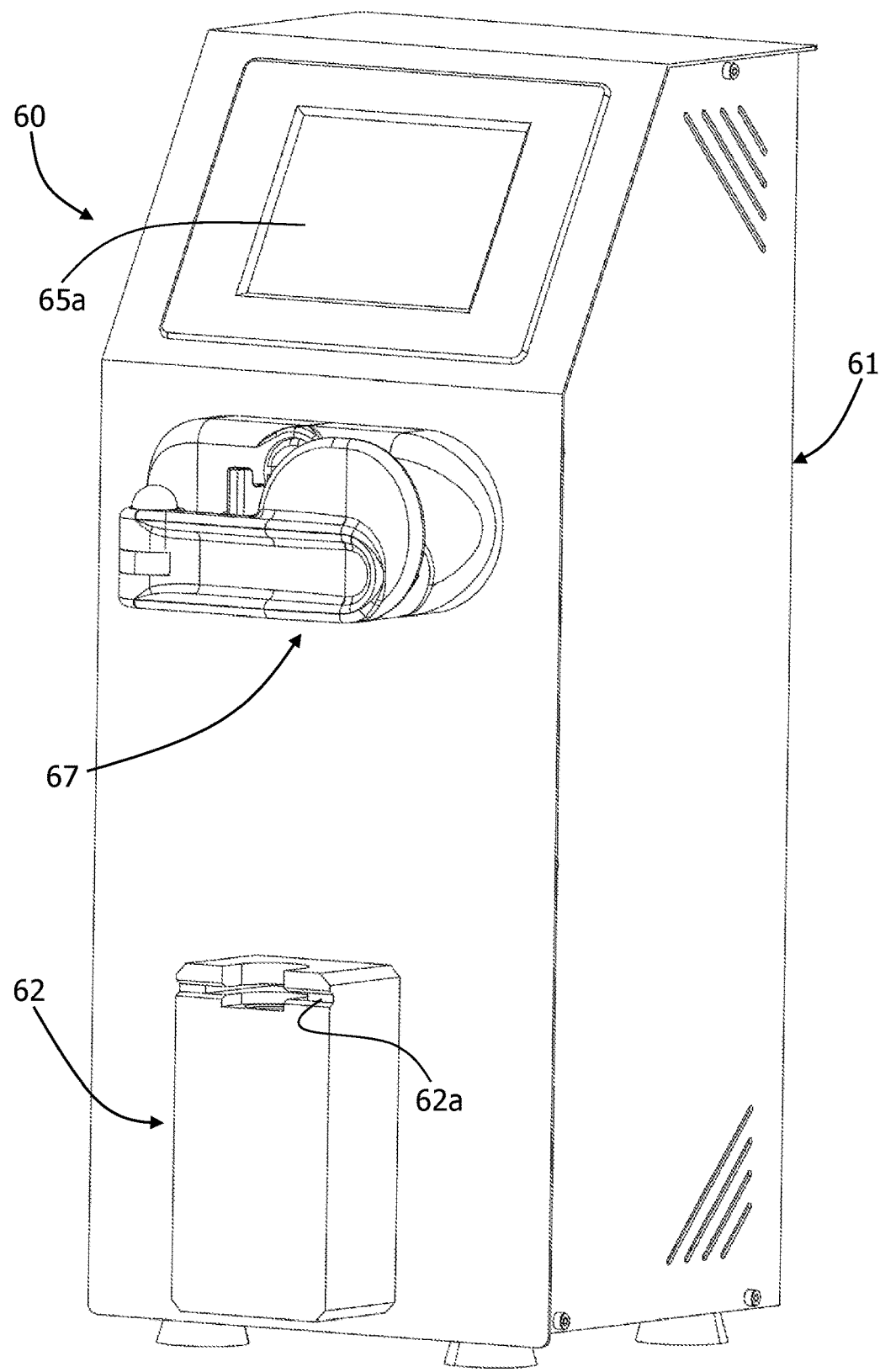
FIG. 6 is a schematic perspective view of an apparatus that can be used in combination with a device according to the invention.
Figure 7:
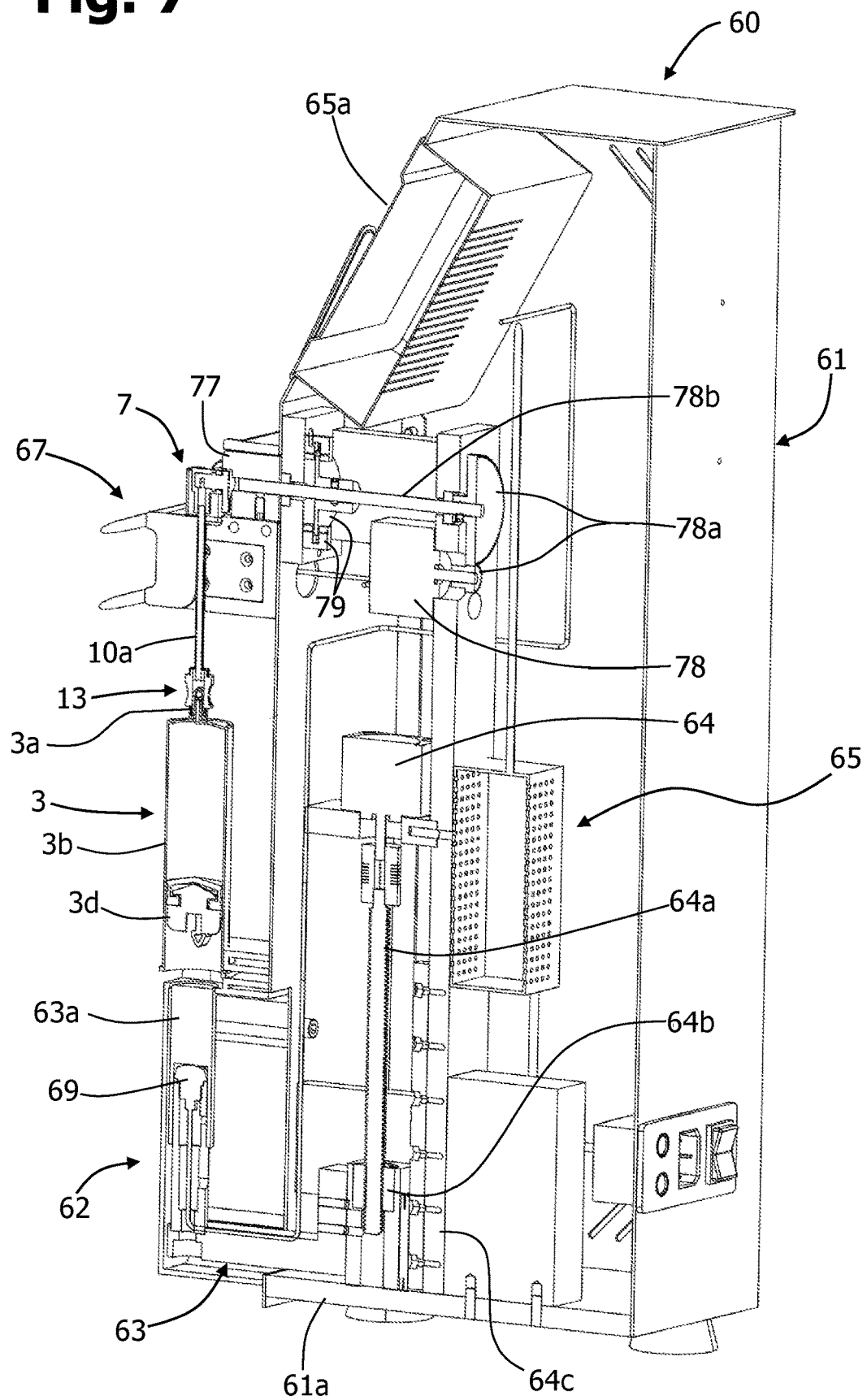
FIG. 7 is a sectioned schematic view of the apparatus of FIG. 6, with a device according to FIG. 2 mounted thereon.

From FIG. 5, it may be appreciated how, in the embodiment illustrated, the construction of the automatically operated valve 12 is basically similar to that of the valve 14a-14b just described, the teachings of which are considered hence as referring also to the valve 12. In this case, the spring 12b of the valve 12 tends to keep the corresponding open/close element 12a in the position for closing of the branch of the line downstream of the way 7b of the deviator valve, whereas in the presence of a flow with suitable pressure, the open/close element 12a can recede, countering the action of the spring 12b. Preferably, also in this case, the force of the spring 12b and the weight of the open/close element 12a and their arrangement, preferably with elements of the valve 12 arranged along an axis transverse to the axis of the syringe 3, are predefined in such a way as to keep the open/close element 12a in the closing position also during the centrifugation steps. Also in this case, the open/close element 12a is preferentially shaped in a way such that in the presence of a possible flow in an opposite direction (from the branch 4a of line), the pressure of the fluid will contribute to keep the open/close element itself in its closing position, illustrated in FIG. 5.

The structure illustrated for the valve 12 and/or the valve 14a-14b, here substantially a one-way valve, or non-return valve, or automatic-closing valve (or self-closing valve), is to be understood merely by way of example, given that this valve can have any structure suited for the purpose, for example with an open/close system constituted by an elastically deformable membrane, designed to open and close a port or provided at the centre with a port designed to open elastically when the membrane is urged by a flow or a pressure in one direction and designed to close elastically as this flow or pressure ceases, or else close when the membrane is urged by a flow or a pressure in the opposite direction. A membrane of this sort is preferably made of elastomer and/or has an elasticity such as to perform functions similar to the ones of the spring 14b, 12b described previously.

Once again in FIG. 5 the deviator valve 7 is visible, with a substantially T-like arrangement of the ways 7b, 7c, and 7d, i.e., with the ways 7c and 7d set at 180° with respect to one another, and the way 7b set at 900 with respect to the ways 7c and 7d. The way 7b is connected to the tube 10a, whereas the way 7c defines directly or is associated to a fast attachment for connection to the attachment 5a of the syringe 5. In a possible embodiment, the way 7c defines or has associated an attachment of a Luer type for connection to the syringe 5; alternatively, other types of coupling may be envisaged (screw coupling, bayonet coupling, snap-in coupling, etc.).

According to a variant not represented, associated to the way 7c is a automatic-closing valve similar to the valve 12, in particular in order to close or keep closed the way 7c upon detachment of the syringe 5. The open/close element of this valve may be kept open by the presence of the syringe 5 and/or be opened by the thrust of a moving fluid, such as the buffy coat or the plasma.

The way 7d of the valve 7 includes or has associated a respective part of the connector 11, which is preferentially a threaded or snap-in connector. The other part of the connector 11 is, instead, associated or defined in the body of the valve 12, and/or connected to the tube 4a. Operative within the valve 7 is an open/close or deviator member 7e, which can be switched by means of the control element 7a, in particular via rotation. In the example, since the valve 7 is a three-way valve, the open/close element 7e preferably defines a T-channel; this channel may on the other hand be of some other type, for example a Y-channel (three stretches of channel at 120° with respect to one another) or an L-channel (just two stretches of channel at 90° with respect to one another).

As has been mentioned, the treatment container 3 is preferentially a syringe, hence with a rigid structure, comprising a generally elongated container body or barrel, designated by 3b in FIG. 3, and a plunger, associated in a movable way to the barrel 3b. As may be seen in FIG. 3, the plunger includes a plunger stem 3c and a plunger head 3d. The plunger head 3d is slidably engaged in a fluid-tight way within the barrel 3b, to define therewith a chamber for collection of the medullar blood, which is in communication with the port 3a. The plunger stem 3c is displaceable in the barrel 3b to move the plunger head 3d and thereby vary the volume of the collection chamber so as to introduce the fluid therein or expel it therefrom accordingly.

The stem 3c and the head 3d of the plunger are separably or releasably coupled to one another, via a coupling arrangement that preferentially comprises first coupling means, at a distal end of the stem, and second coupling means, on a face of the plunger head that is opposite to the port 3a. The aforesaid coupling arrangement may be of any type known in the field, for example with a bayonet coupling, a threaded coupling or, in general, an arrangement in which coupling and uncoupling between the stem and the head is obtained via angular movement of the former with respect to the latter. In a preferred embodiment of the invention, the aforesaid arrangement is obtained according to the Italian patent application No. TO2013A000924 filed in the name of the present applicant, the teachings of which are incorporated herein for reference. In a solution of this sort, release between the stem 3c and the head 3d of the plunger, i.e., release between the aforesaid first and second coupling means, can be obtained by operating a manoeuvring rod, designated by 3e in the figures, slidably mounted in a corresponding axial seat of the stem 3c.

In a preferred embodiment, at least one step of the separation or enrichment method is performed with the aid of an automated apparatus, in particular for controlling automatically operation forwards of the plunger head 3d of the syringe 3, operation of the valve 7, and detection of passage of the buffy coat in the tube 10a.

A possible embodiment of an automated apparatus is schematically exemplified in FIGS. 6-12, where the apparatus is designated as a whole by 60. In the case exemplified, the apparatus 60 performs the functions of separating in an automated way the fraction of poor plasma from the other separated fractions of blood or medullary aspirate and then isolating the total fraction of stem or stromal cells, i.e., the buffy coat, from the red blood cells.

The apparatus 60 has a load-bearing structure or body 61, provided with a support 62 for housing and/or positioning and/or actuation of the syringe 3. In the example represented, this support 62 is located at the front and configured for setting the syringe 3 vertically, i.e., with the attachment 3a upwards. In the example, the support 62 includes a slit or seat 62a for receiving a flange 3b' of the barrel 3b of the syringe 3 (FIG. 1), from which the corresponding stem 3c has been previously removed, as mentioned previously. Movable inside a hollow part of the support 62 is an actuation member 63a, visible for example in FIG. 7, designed to move in a controlled way the plunger head 3d of the syringe 3. As may be seen in FIG. 7, the actuation member 63a belongs to a structure 63, which is vertically movable in opposite directions with respect to a base 61a and is operated via an actuator 64. The actuator 64 may, for example, be an electric motor with screw shaft 64a, associated to which—for example via a volute 64b—is the structure 63 so that the latter can be displaced vertically in a guided way; in the example, the structure 63 has a part configured substantially like a slide, coupled to a corresponding vertical guide 64c.

The position of the structure 63, and hence of the actuation member 63a, can be controlled via suitable sensors that form part of the control system of the apparatus, which is designated as a whole by 65, or else are connected thereto. The control system 65, the program or software of which supervises general operation of the apparatus 60, includes suitable control means, for example a programmable logic circuit (PLC) or an electronic circuit with microcontroller, and user-interface means, for example a display 65a of a touch-screen type, for entering the commands and operative parameters required.

Preferentially, the apparatus 60 also includes a device 67 for housing an electromagnetic or optical sensor system, preferably a transparency or opacity sensor, and/or for valve means of the device 1. Preferably, the device 67 is also prearranged for performing functions of positioning and support of elements of the device 1, such as for example the tube 10a (for the purposes of electromagnetic or optical detection) and/or the valve 7 and/or the valve 12 and/or the syringe 5.

Figure 11:
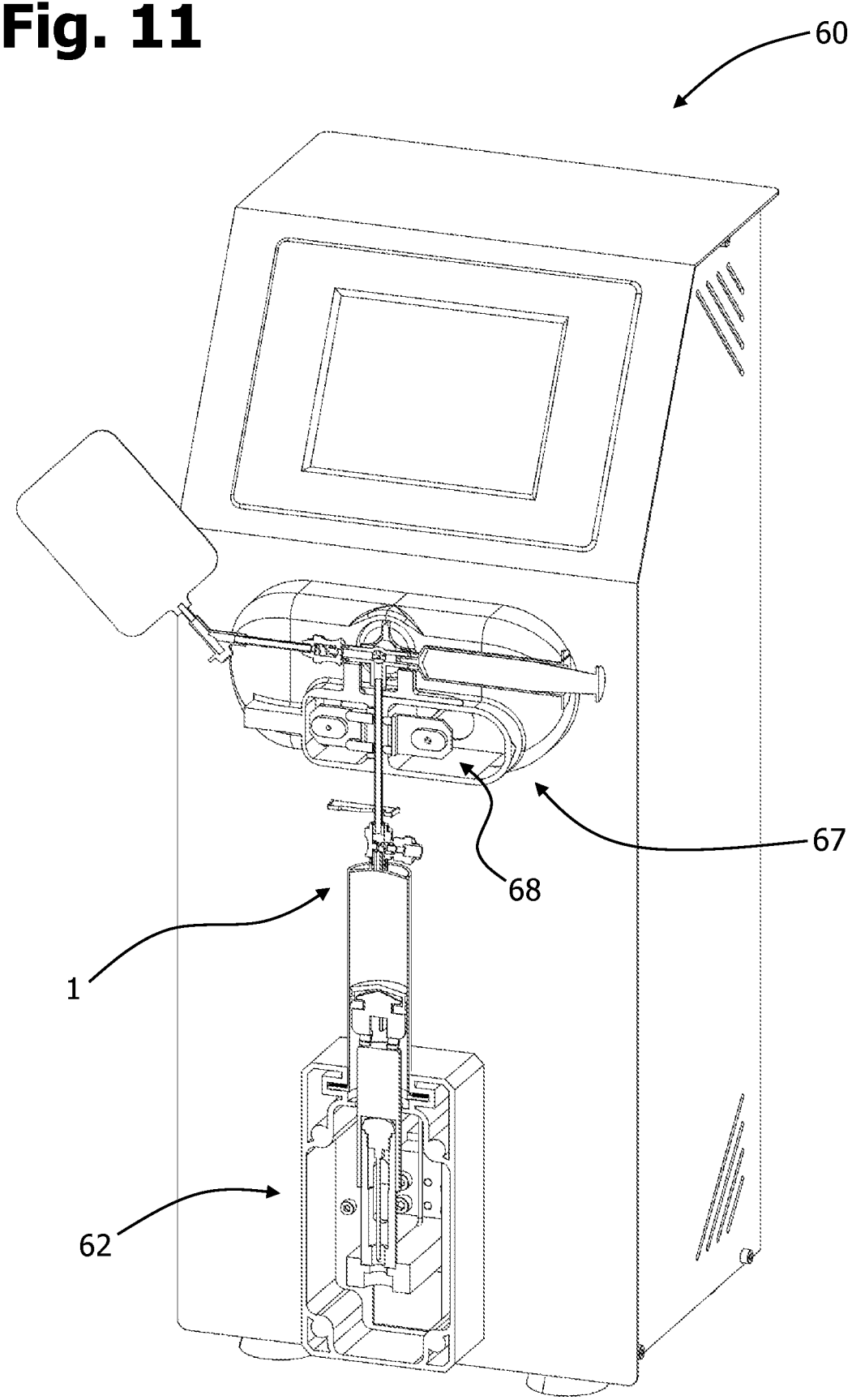
FIG. 11 is a view similar to that of FIG. 10, with two parts of the apparatus partially sectioned.
Figure 12:
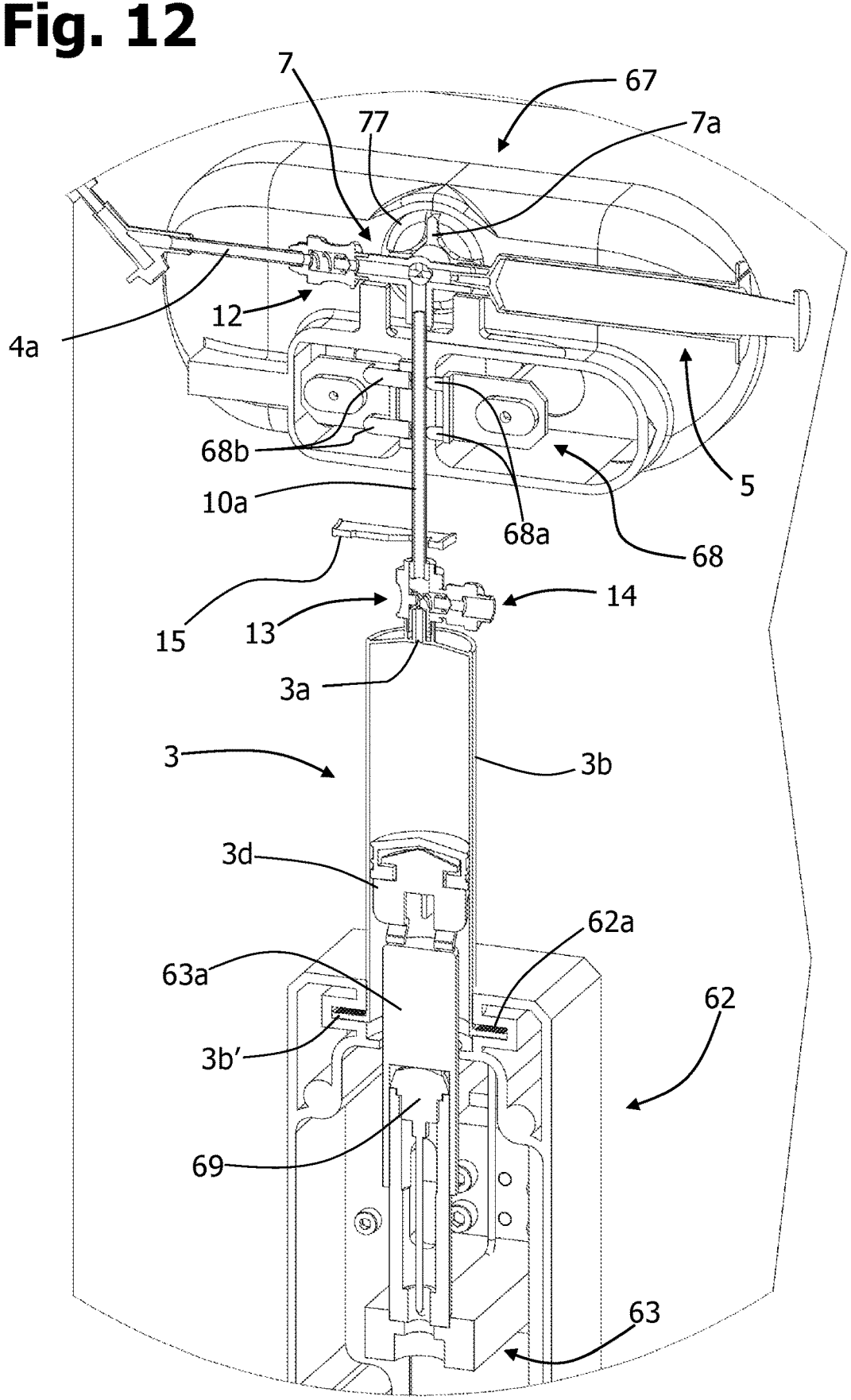
FIG. 12 is a detail at an enlarged scale of FIG. 11.

The aforesaid sensor system, designated by 68 in FIGS. 11 and 12, includes at least one emitter and at least one receiver of electromagnetic radiation, for example light. In one embodiment, there is provided an emitter of a signal at a predefined wavelength and a receiver designed to detect the aforesaid signal and/or its variations. Preferably, the sensor system is devised for transmitting the electromagnetic signal through a stretch of a line or tube of the device 1 that is transparent to the aforesaid signal, where the signal varies at the receiving end (for example, it is attenuated or in any case altered) according to the composition of the flow in the tube. For instance, the presence or passage of a larger amount or concentration of given substances or particles in the fluid (such as red and/or white blood cells and/or stem cells and/or platelets) in the stretch of tube set between the transmitter and the receiver prevents or attenuates or in any case varies the passage of the signal between the transmitter and the receiver, this signal variation hence indicating the composition of the flow.

Alternatively, the sensor system 68 is devised for transmitting an electromagnetic or light signal that is at least in part deviated and/or refracted and/or reflected by the presence of substances or particles in the fluid. As in the previous case, the passage of a different composition or larger amount or concentration of given substances or particles in the fluid in the aforesaid stretch of tube determines a different refraction and/or reflection of the signal that can be detected at the receiving end, which indicates, for example, transition between different layers or fractions.

The sensor system can also be prearranged for detecting the colour of the flow, for example on the basis of detection of light absorption by substances or particles present in the fluid.

Figure 9:
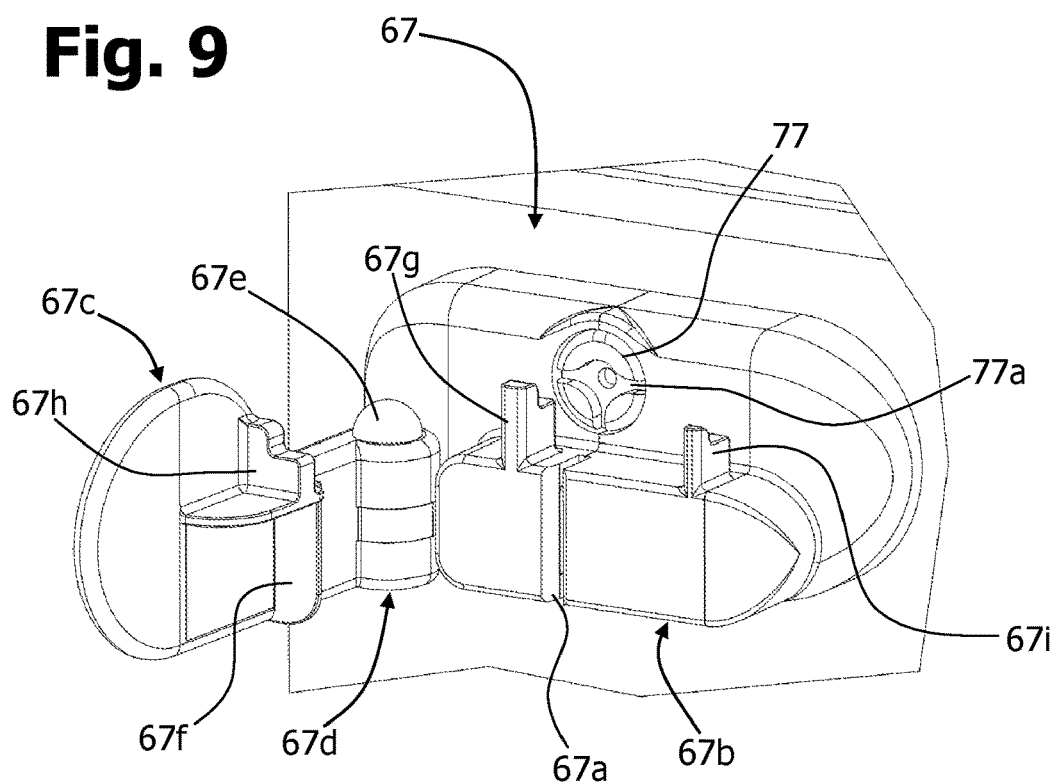
FIG. 9 is a view similar to that of FIG. 8, with the particular of the apparatus in a second condition.

The support 67 is shaped so as to define a passage or seat 67a-visible for example in FIG. 9—in which there may be inserted or positioned a stretch of the tube 10a. In this seat 67a, preferably mounted on angled or opposite parts are the aforesaid emitter (for example a light-emitting diode or LED) and receiver (for example, a photoresistor or a phototransistor). Preferably, two optical sensors are provided in sequence or in series with respect to one another, such as a pair of emitters in sequence and a pair of corresponding receivers in sequence, designated by 68a and 68b in FIG. 12. The distance between the emitters, on one side, and the receivers, on the other side, i.e., the distance between two optical sensors in sequence, is predefined and may, for example, be approximately 10 mm.

Figure 8:
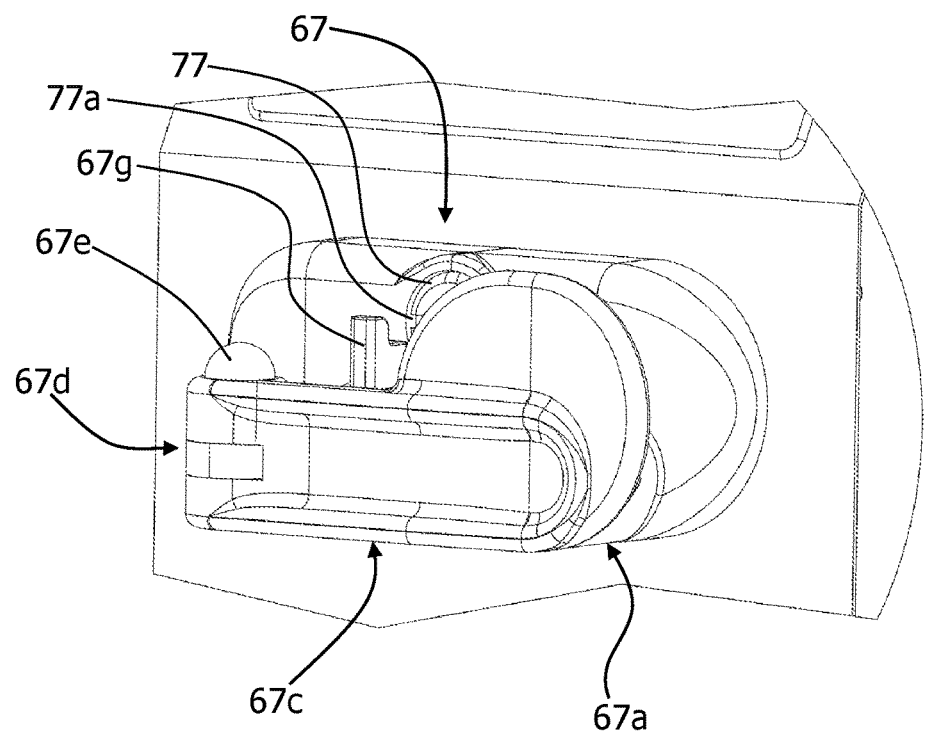
FIG. 8 shows a detail at an enlarged scale of the apparatus of FIG. 6, regarding a particular of the apparatus in a first condition.

In one embodiment, as may be seen in FIGS. 8 and 9, the support 67 comprises a casing 67b that defines the vertical seat 67a, associated to which is a movable lid 67c. Preferentially, the lid 67c is articulated to the casing 67b by way of a hinge 67d, very preferably with vertically rotating pin 67e. Preferentially, means are provided for urging and/or keeping the lid 67c in a respective closed position, i.e., a position in which at least one portion of the back of the lid itself is set up against a corresponding portion of the front of the casing 67b, in particular in the seat 67a. These means may, for example, comprise a spring integrated in the hinge 67d. Another possibility is to provide one or more permanent magnets associated to one of the lid 67c and the casing 67b, which are able to attract one or more ferromagnetic elements associated to the other one of the lid 67c and the casing 67b. Preferentially, the lid 67c is shaped in such a way as to push and/or position a corresponding stretch of the tube 10a within the seat 67a, in a position corresponding to the sensor system 68. In the example illustrated, for this purpose, the side of the lid 67c facing to the seat 67a is provided with a shaped relief, represented schematically and designated by 67f in FIG. 9.

In one embodiment, a support 67—which does or does not integrate the optical sensor system—is shaped also to define supporting and/or positioning means for the valve 7, which can be associated to or defined by the casing 67b and/or associated to or defined by the lid 67c. Two of such supports are designated by 67g and 67h in FIGS. 8 and 9. Preferentially, the supporting means, such as the supports 67g and 67h, are configured for supporting the valve 7 and/or keeping it in position during operations thereon, such as the movement of its control element 7a.

In one embodiment, a support 67—integrating or not the optical sensor system and/or the supporting means of the valve 7—is shaped to define supporting and/or positioning means for the syringe 5 and/or for the corresponding attachment 5a. The aforesaid supporting means for the syringe 5 can be associated to or defined by the casing 67b and/or the lid 67c.

One of the above supports may, for example, be the aforesaid element in relief 67h associated to the lid 67c, which may advantageously be configured for supporting (also) the attachment 5a and/or at least one end portion of the syringe 5, as may be seen for example in the cross section of FIG. 11.

Figure 10:
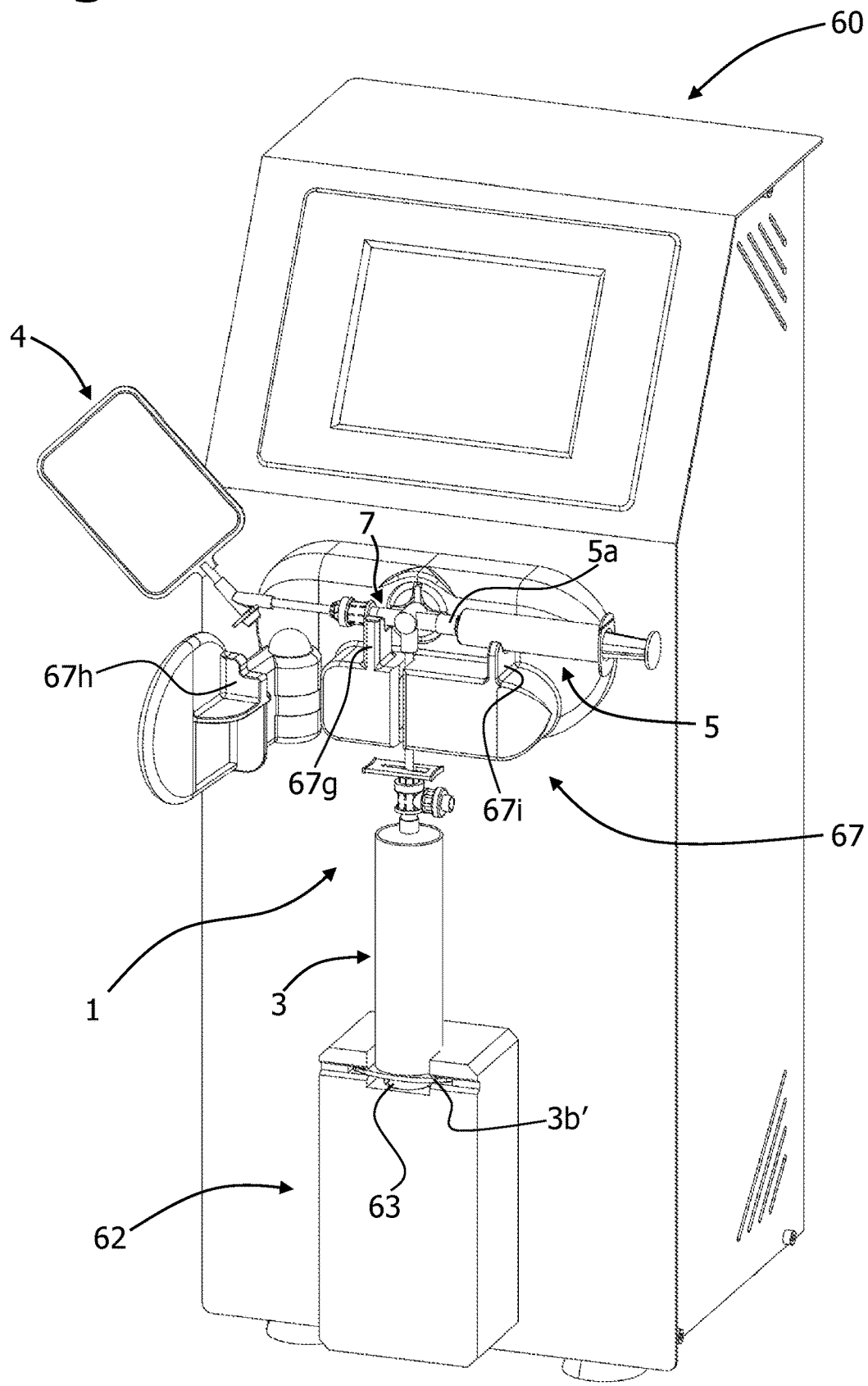
FIG. 10 is a view similar to that of FIG. 6, with a device according to FIG. 2 mounted on the apparatus.

A further supporting and/or positioning element 67i for the syringe 5 may be seen in FIGS. 9 and 10, associated or defined by the casing 67b so as to couple to and/or support the casing of the syringe 5 in an intermediate position thereof and/or in a position opposite to the attachment 5a (the representation of the element 67i has been omitted in FIGS. 11 and 12).

Preferably, the supports 67h and 67i are configured for supporting and/or keeping the syringe 5 in a substantially horizontal position, even though they may, however, be alternatively configured for keeping the syringe 5 in a different angled or vertical position, in particular when a flexible tube is set between the syringe 5 and the valve 7.

With reference once again to FIG. 7, in a preferred embodiment, operative within the actuation member 63a is a sensor 69, for example a microswitch, used by the system 65 for the purposes of control of the position of the member 63. In particular, the sensor 69 has the function of detecting the mechanical contact between the top of the member 63a and the plunger head 3d of the syringe 3, when the member 63a is raised via the corresponding actuation system.

Preferably, at least one part of the sensor element 69 contributes to transmitting the movement or thrust of the actuator 64 to the member 63a.

In an advantageous embodiment, also a further actuation system is provided, controlled by the control system 65 of the apparatus 60, for controlling in an automated way switching of the valve 7 among at least some of its possible operating positions.

For this purpose, the control element 7a of the valve 7 may be shaped for coupling to a corresponding actuation member, preferably provided with a seat with a shape that is at least in part complementary to that of the control element. An example of this further actuation system may be seen in FIG. 12, where designated by 77 is a rotary member, to which there can be coupled the control element 7a of the valve 7. The actuation element 77 can be operated via a corresponding actuator 78, visible in FIG. 7, such as an electric motor with rotary shaft. In the example illustrated the shaft of the motor 78 drives, via a gear coupling 78a, a rod 78b, associated to which is the element 77. The rotary element 77 has preferentially a seat or indentation 77a (FIG. 9) designed to receive at least partially the control element 7a, at least to the extent where it is possible to impose a rotation thereon. In the example, this seat 77a is recessed and is at least in part complementary to the control member 7a of the valve 7, which is preferably provided with radial reliefs or lobes and/or has a shape such as that it can be operated either manually or in an automated way. Evidently possible are other embodiments useful for obtaining rotation of the control element 7a via the rotary element 77.

Preferentially, at start of an operating cycle of the apparatus 60, the member 77 has an angular position such that the control element 7a of the valve 7 can be coupled in the seat 77a only when the open/close element of the valve itself is in a predefined position, for example a position such that the open/close element 7e sets in communication the ways 7b and 7d, i.e., sets in communication the container 3 with the container 4. For this purpose, in a preferred embodiment, associated to the actuation system of the element 77 is an angular-position detection system of any known type, such as an encoder system, designated by 79 in FIG. 7, interfaced with the control system 65.

A possible methodology of use of a device 1, in particular for the purposes of separation and concentration of stromal or stem cells from venous blood or from medullary aspirate, is described hereinafter. It is assumed, for this purpose, that the device 1 is supplied already assembled, or else it is assembled in the condition represented in FIG. 1 at the moment of use, preferably in sterile environment. It will be assumed, merely by way of example, that the syringes 2, 3 and 5 have a capacity of 60 ml, 30 ml, and 10 ml, respectively.

As previously mentioned, the device according to the invention may be used for treatments starting from medullary aspirate or else for treatments starting from venous blood, in which case the sampling device used may be of the type designated by $K_1$ or else of the type designated by $K_2$, respectively. Consequently, in what follows, the sampling methodology will be described with reference to the two possible cases of sampling of medullary blood and of venous blood.

1. The medullar or venous blood is taken from the patient, with modalities of themselves known. For instance, in the case of use of the device $K_1$, the Jamshidi needle with the corresponding mandrel is introduced into the iliac crest of the patient, with small rotary movements; once the bone has been reached, the mandrel of the needle is removed, and the needle is made to penetrate into the bone for approximately 1.5 cm.

2. Once again with reference to the case of sampling of medullar blood, the attachment 2a of the syringe 2, preferentially previously moistened with heparin, is coupled to the corresponding attachment of the biopsy needle of the device $K_1$, introduced into the iliac crest. Via the syringe 2 a certain amount of medullar blood, for example 25 ml, is aspirated. The attachment 2a of the syringe 2 is then disconnected from the biopsy needle of the device $K_1$. With reference, instead, to the case of sampling of venous blood, the attachment 2a of the syringe 2 can be coupled to the tube of the device $K_2$, provided with suitable attachment, or else directly to a hypodermic sampling needle, for direct sampling of blood from a vein of the patient.

3. Associated to the attachment 6a of the syringe 6 is a hypodermic sterile needle (not represented), and via the syringe itself a certain amount, for example 5 ml, of anticoagulant (ACD) is drawn from a corresponding container.

4. After prior removal of the corresponding needle, the attachment 6a of the syringe 6 containing the anticoagulant is coupled to the attachment 14 of the connector 13. After prior closing of the tube 10a by way of the clamp 15, the anticoagulant is drawn from the syringe 6 via the syringe 3 or else injected with the syringe 6 into the attachment 14 and hence into the syringe 3, in this step the open/close element 14a of the valve 14a-4b opening automatically. At the end of the operation, the syringe 6 is removed from the attachment 14, which is reclosed automatically by the open/close element 14a.

5. The attachment 2a of the syringe 2, containing the medullar or venous blood, is coupled to the attachment 14, and the contents of the syringe are transferred into the syringe 3 in which the anticoagulant had been previously collected. In this step, the clamp 15 is kept in the position for closing of the tube 10a. The medullar or venous blood is drawn from the syringe 2 via the syringe 3 or else injected with the syringe 2 into the attachment 14, and hence into the syringe 3, in this step the open/close element 14a opening automatically. Once the operation of transfer of the medullar or venous blood from the syringe 2 to the syringe 3 is through, the syringe 2 is separated from the attachment 14, which is reclosed automatically by the open/close element 14a.

In a variant, operations similar to the operations 2 and 5 can be repeated—in any case after the operations 3-4 have been carried out—using at least one further syringe similar to the one designated by 2, in the case where it is desired to treat with the syringe 3 a total amount of medullar or venous blood greater than the capacity of a single syringe 2. In this case, the further syringe or syringes 2 are also preferably in a sterile package.

At the end of the operation or of the last operation of sampling of the blood, the biopsy needle can be removed from the skin of the patient. After the last transfer of medullar or venous blood into the syringe 3 the attachment 14, albeit already closed by the open/close element 14*a*, is preferably plugged with an anti-drip plug, which is also supplied along with the device 1.

6. The stem 3*c* of the syringe 3 is released from the corresponding head 3*d* and the device 1 (hence the modules A, B, and the syringe 5 still connected together) is put on the rack of the centrifuge machine.

The syringe 3 (i.e., its barrel 3*b* with the head 3*d*) is preferably put on the rack in a substantially vertical position, for example with the aid of a corresponding support or adapter, preferably a rocking one or one designed to vary the position during centrifugation, which is possibly shaped so as to guarantee positioning also of other parts of the device 1, such as the module B and the syringe 5.

For the purposes of carrying out this step, the presence of the flexible tubes 10*a* and 4*a* (and of the possible flexible tube for connection of the syringe 5 to the valve 7) is advantageous in so far as they enable the various parts to be positioned according to the need on the rack of the centrifuge machine and/or on the aforesaid support.

Centrifugation at a relatively low speed (for example, 1400 rpm for 9 minutes) is then carried out in order to cause separation between parts of the mixture of whole blood and anticoagulant contained in the syringe 3, in particular to obtain a sedimentation substantially in a number of layers, one of which comprising plasma, another comprising the buffy coat, and another comprising red blood cells, as a result of their different density or different weight. In this way, in the variable-volume chamber of the container 3 there will be present a layer of sediment comprising red blood cells, an intermediate layer comprising the buffy coat, and a supernatant layer comprising plasma and platelets.

Following upon centrifugation, the layer of sediment is closer to the head 3*d* of the plunger of the syringe 3, whereas the supernatant layer is comprised between the layer of buffy coat and the wall of the barrel 3*b* equipped with the attachment 3*a*; the layer of buffy coat is comprised between the layer of sediment and the supernatant layer.

7. The barrel 3*b* of the syringe 3 containing the separated blood is coupled to the support 62 of the apparatus 60, so that the tube 10*a* passes through the seat 67*a* and the control element 7*a* of the valve 7 is in the housing 77*a* of the actuation element 77. For the purposes of execution of this step, the lid 67*c* of the support 67 must be open, as for example in FIG. 9 or FIG. 10. After the positioning described, the lid can be reclosed. After closing, the supports 67*g*, 67*h*, and 67*i* guarantee positioning of the body of the valve 7 and of the syringe 5.

8. After the syringe 3 without its stem 3*c* has been coupled to the support 62, and after—via the user interface 65*a*—the parameters possibly required have been entered and a command for cycle start has been imparted, the actuator 64 of the apparatus 60 is operated so as to move the structure 63 from beneath upwards, for example starting from a lowered end-of-travel position. In the case where the predefined position for the valve 7 is that of closing between the ways 7*b* and 7*d*, the system 65 preliminary drives—via the actuation system 78, 78*a*, 78*b* and the corresponding sensor system 79—rotation of the member 77 in order to bring the valve itself into the position of opening between the ways 7*b* and 7*d* and closing of the way 7*c*.

At a certain point of raising of the structure 63, the control system 65 detects, via the sensor 69, the contact between the member 63*a* and the plunger head 3*d*, in this way acquiring information regarding the position of the head itself. Detection of this position may, for example, be useful to enable first a relatively fast advance of the member 63*a* and then a slower movement thereof, following upon contact between the member 63*a* and the head 3*d*. The sensor 69 thus enables detection of the position of effective start of travel or thrust on the plunger head 3*d*, and hence automatic detection of the effective travel or distance of movement of the head itself.

After contact, the member 63*a* then starts to bring about displacement of the head 3*d*, which can also be controlled at different speeds, for example with an initial, faster, step and a final, slower, step. During movement of the plunger head 3*d* the flow within the tube 10*a* undergoes scanning or detection by the electromagnetic or optical system 68, in particular so as to measure at least one electromagnetic or optical characteristic (such as transmittance, refraction, or reflection) of the moving fluid, preferably in two points of the tube 10*a* set at a distance from one another (in a way corresponding to the distance between two sensors, such as the distance existing between the emitters 68*a* and the receivers 68*b* of each pair). Preferentially, the control electronics 65 makes an automatic calibration with respect to the value detected by the optical system upon turning-on of the apparatus 60, before and/or after positioning of the device 1 on the apparatus.

By operating the plunger head 3*d* a transfer into the bag container 4 of part of the contents of the syringe 3 is brought about. In particular, the head 3*d* is made to advance so as to transfer the plasma alone, or a portion thereof, from the syringe 3 to the bag container 4. In this step, the valve 14*a*-14*b* integrated in the connector 13 is automatically closed and prevents any exit of the plasma from the attachment 14, whereas the valve 12 is opened automatically by the thrust or pressure exerted by the plasma on the open/close element 12*a*.

When the plasma starts to flow as a result of the thrust exerted by the member 63*a* on the plunger head 3*d*, the optical system 68 detects a first variation of the optical characteristic considered (for example, transmittance), when the air-plasma transition reaches the optical system 68 on the tube 10*a*, and a second variation of the same optical characteristic upon passage of the buffy coat, i.e., when the transition from plasma to buffy coat reaches the optical system 68 on the tube 10*a*: the control system 65 then interrupts operation of the actuator 63, 64, and hence of the member 63*a*, when both of the receivers 68*b* of the system have detected the presence of the buffy coat, or else interrupts operation after a pre-set delay time or a further pre-set travel of the actuator 63, 64.

Sampling of the signal may, for example, be carried out at a frequency of approximately 1 kHz, corresponding, for example, to a displacement of the fluid of approximately 50 μm between one sampling and the next. When the control system 65 detects via the optical sensor 68 the aforesaid second variation of the optical characteristic considered, which indicates start of flow of the buffy coat, or in any case at the appropriate predefined or calculated moment, also the actuator 78 associated to the member 77 is operated so as to turn the control element 7*a* of the valve 7 in order to bring its open/close element into the position of connection between the ways 7*b* and 7*c*, and of occlusion of the way 7*d*.

The control system 65 then starts again operation of the actuator 64, and hence of the member 63*a*, thus conveying the buffy coat towards the syringe 5. For the purposes of control of transfer of the buffy coat into the syringe 5 and/or for the purposes of safety, the sensor system 68 may detect also a third variation of the optical characteristic considered, when the transition from buffy coat to red blood cells reaches the optical system 68 on the tube 10*a*, possibly interrupting transfer (for example, if the predefined amount has been delivered or else for the purposes of safety if the amount of buffy coat available is less than the parameter or amount of buffy coat set by the user for the transfer).

As may be seen, then, the apparatus 60 conveys automatically the plasma poor in platelets into the bag container 4 and then the buffy coat into the syringe 5. The amount of buffy coat that is to be transferred from the syringe 3 to the syringe 5 may possibly be set by the operator.

9. At this point, after prior closing of the connection between the ways 7*b* and 7*c* by turning the control element 7*a* of the valve 7 or via a possible automatic valve on the attachment 7*c*, the syringe 5 containing the buffy coat can be detached from the rest of the device 1 and used for applying the buffy coat to the patient.

The module B, which comprises the bag 4 containing the plasma, and the module A, which comprises the syringe 3 containing the possible residue of buffy coat and the red blood cells, can be separated via the connector 11 and disposed of, or else the respective contents can be used for other applications.

The disposable needles used are preferentially provided along with the other components of the device 1, in a sterile package.

Figure 13:
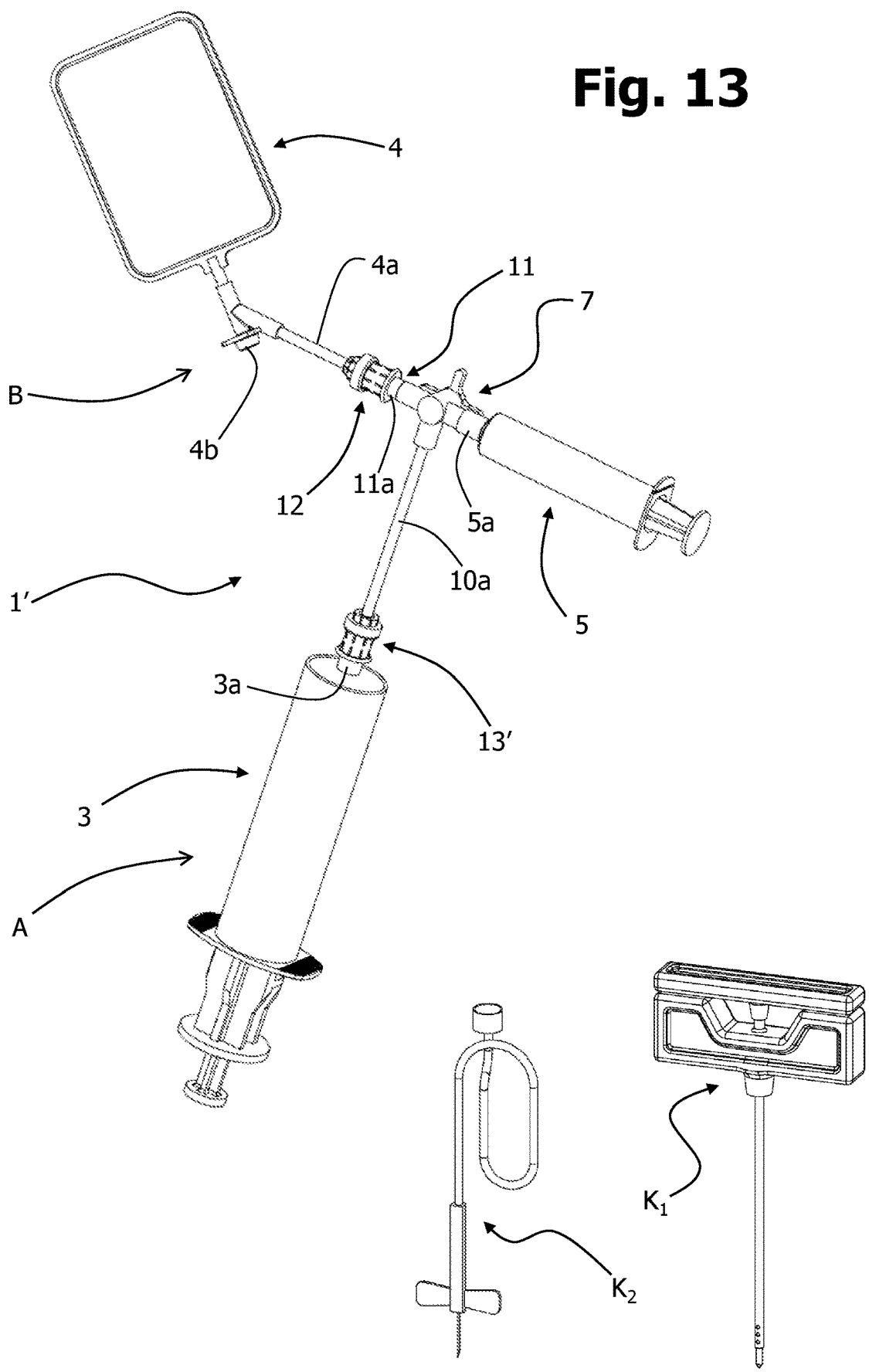
FIG. 13 is an exploded schematic view of a medical device according to a further embodiment to the invention.

FIG. 13 illustrates a second version of a device according to the invention. In this figure, the same reference numbers are used as those of the previous figures to refer to elements technically equivalent to the ones already described previously. As may be noted, the device 1' of FIG. 13 differs from that of FIGS. 1-3 basically owing to the absence of the syringes 2 and 6, the fact that the three-way connector 13 on the branch 10*a* of line is here replaced by a simple attachment, for example of a Luer type, its releasable coupling to the attachment 3*a* of the syringe 3, and the absence of the clamp 15.

A possible mode of use of the device 1' is described in what follows.

For the purposes of sampling of the medullar or venous blood from the patient the same operation as the one described in point 1 above is carried out, using the device $K_1$ or else the device $K_2$ (or, for the venous blood, a hypodermic needle).

The syringe 3 is separated from the device 1' and coupled to its attachment 3*a* is a hypodermic sterile needle, via which an amount of anticoagulant is drawn from a corresponding container into the syringe itself. The needle is then removed from the syringe 3, and the attachment 3*a* of the latter is coupled to the needle of the device $K_1$, for medullar sampling, or else to the tube of the device $K_1$ or directly to a hypodermic needle, for venous sampling.

Via the syringe 3, which now contains the anticoagulant, the desired amount of blood is aspirated. Next, the syringe 3 is separated from the device $K_1$ or $K_2$ or from the hypodermic needle.

The stem 3*c* of the syringe 3 is released from the corresponding head 3*d*, and the syringe 3 alone (i.e., its barrel 3*b* with the head 3*d*) is set on the rack of the centrifuge machine, for example via a corresponding adapter or support, as already described previously. The head 3*d* hence remains within the syringe, in the position that it has reached.

After centrifugation, which is carried out with the modalities already described, the syringe 3 containing the separated medullar or venous blood is coupled to the attachment 13', and the device 1' is set on the apparatus 60, with modalities similar to the ones already described in point 7. Then the procedure follows modalities similar to the ones described in points 8 and 9 above. Also in this case the modules A and B can be separated via the connector 11 and disposed of or used for other applications.

Figure 14:
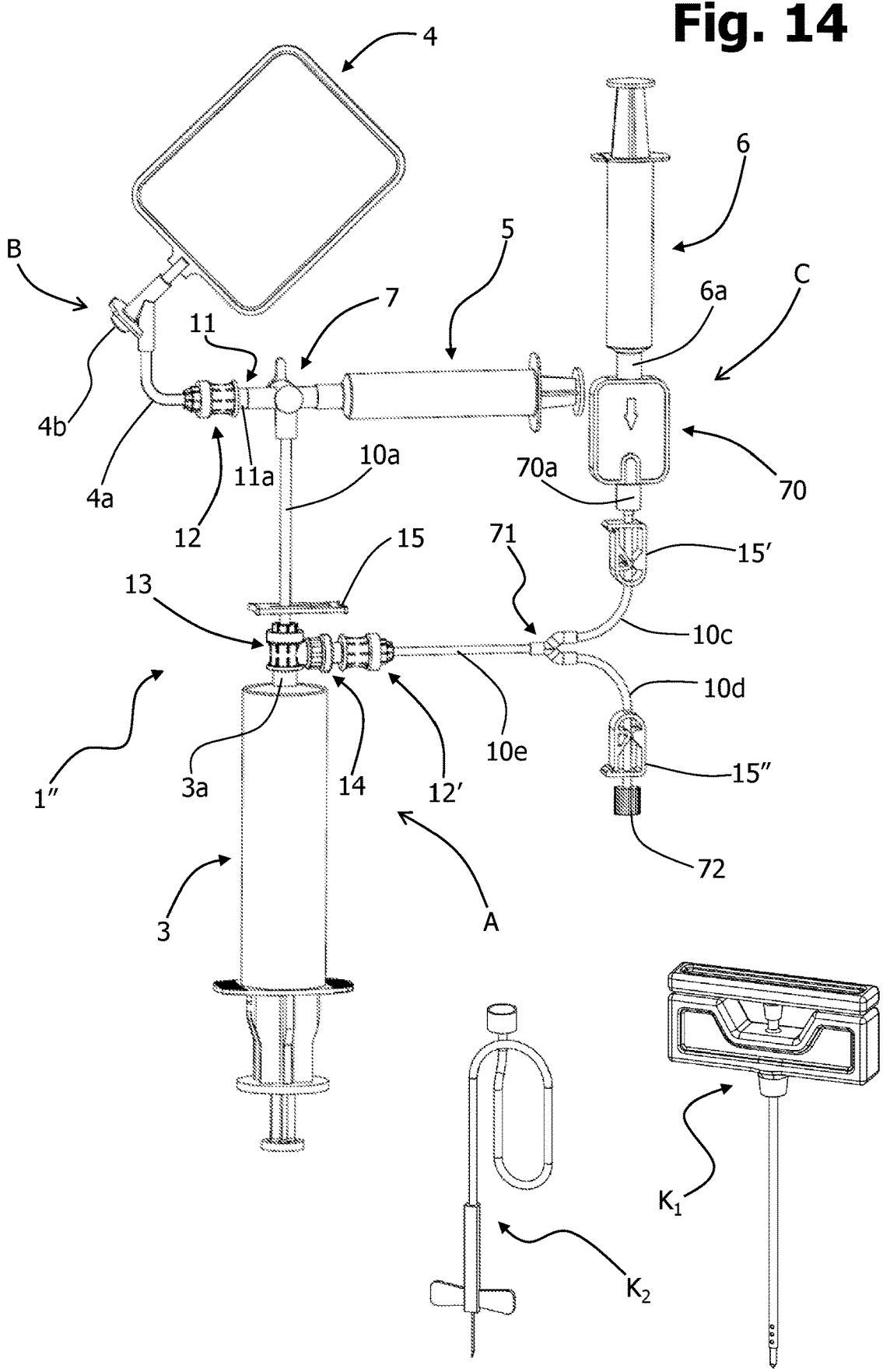
FIG. 14 is an exploded schematic view of a medical device according to a further embodiment to the invention.

FIG. 14 illustrates a third version of a separation device according to the invention. Also in this figure the same reference numbers are used as those of the previous figures to refer to elements that are technically equivalent to the ones already described previously.

The device 1" of FIG. 14 differs from that of FIGS. 1-3 basically in that the syringe 6 forms part of a further module C of the device, which includes additional functional elements.

The module C comprises an antibacterial filter 70, having an inlet attachment (not visible) configured for coupling with the attachment of the syringe 6, for example of a Luer type. Provided at outlet of the filter 70 is an outlet attachment 70*a*, for the ends of a tube or branch of line 10*c*, the opposite end of which is connected to the first inlet of a bifurcation, constituted by a T-connector or Y connector, designated by 71. Preferably provided along the tube 10*c* is a clamp 15', here having a structure different from the clamp 15 but operating in a similar way. Connected to the second inlet of the connector 71 is the end of a tube or branch of line 10*d*, the opposite end of which is provided with an attachment 72, for example of a Luer type, for connection to the sampling device $K_1$ or $K_2$. Also along the tube 10*d* a clamp 15" is preferably provided, here having a structure similar to that of the clamp 15'.

Connected to the outlet of the connector 71 is the end of a further tube or stretch of line 10*e*, the opposite end of which is connected to an attachment 12' that can be coupled to the attachment 14 of the connector 13, in which there could be present a self-closing valve, similar to the valve 12.

A possible mode of use of the device 1" is described in what follows.

For the purposes of sampling of the medullar blood from the patient, an operation substantially similar to the one described in point 1 above is carried out, using the sampling device $K_1$ (medullar sampling) or the sampling device $K_2$ (venous sampling). The syringe 6 can be supplied already with anticoagulant or else, via the syringe 6, a certain dose of anticoagulant is sampled, in a way similar to what has been described in point 3 above. After removal of the needle from the syringe 6, its attachment 6*a* is coupled to the inlet connector of the filter 70. The tube 10*a* is closed by way of the clamp 15, while the clamps 15' and 15" are in the positions of opening and closing, respectively, of the tubes 10*c* and 10*d*. The anticoagulant is then injected via the syringe 6 into the attachment 14, i.e., into the syringe 3, or else drawn in via the syringe 3.

The attachment 72 is then coupled to a corresponding connector of the device $K_1$ or of the device $K_2$: also in this case, hence, drawing of the medullar or venous blood is carried out by means of the syringe 3, by pulling the corresponding stem back. For the purposes of execution of this step, the clamps 15' and 15" must be previously brought into the positions for closing the tube 10*c* and opening and the tube 10*d*, respectively. Next, the module A is separated from the module C and from the sampling device $K_1$ or $K_2$, which is in turn removed from the skin of the patient.

In a variant embodiment, sampling of the medullar or venous blood can be carried out using one or more syringes of the type designated by 2 in FIG. 1. In this case, the syringe 2 used is first coupled to the device $K_1$ or $K_2$ (or directly to a hypodermic needle for venous sampling) and, after blood sampling from the patient, coupled to the attachment 72, in order to transfer the blood sampled into the syringe 3.

Once the sampling operation is through, the module C of the device 1 can be uncoupled from the module A by separating the attachment 12' from the attachment 14. In this step, the possible valve associated to the attachment 12' prevents exit from the tube 10e of any blood that may still be present therein. The attachment 14 is preferably plugged using the anti-drip plug provided.

The stem 3c of the syringe 3 is released from the corresponding head 3d, and the modules A and B of the device 1" that are still connected together are put on the rack of the centrifuge machine, as has been already described previously in point 6.

The device 1", i.e., its modules A and B coupled together, is then set in the apparatus 60 with modalities similar to the ones already described in point 7. The procedure then follows modalities similar to the ones described in points 8 and 9 above. Also in this case, the modules A and B can be separated via the connector 11 and disposed of or used for other applications.

Figure 15:
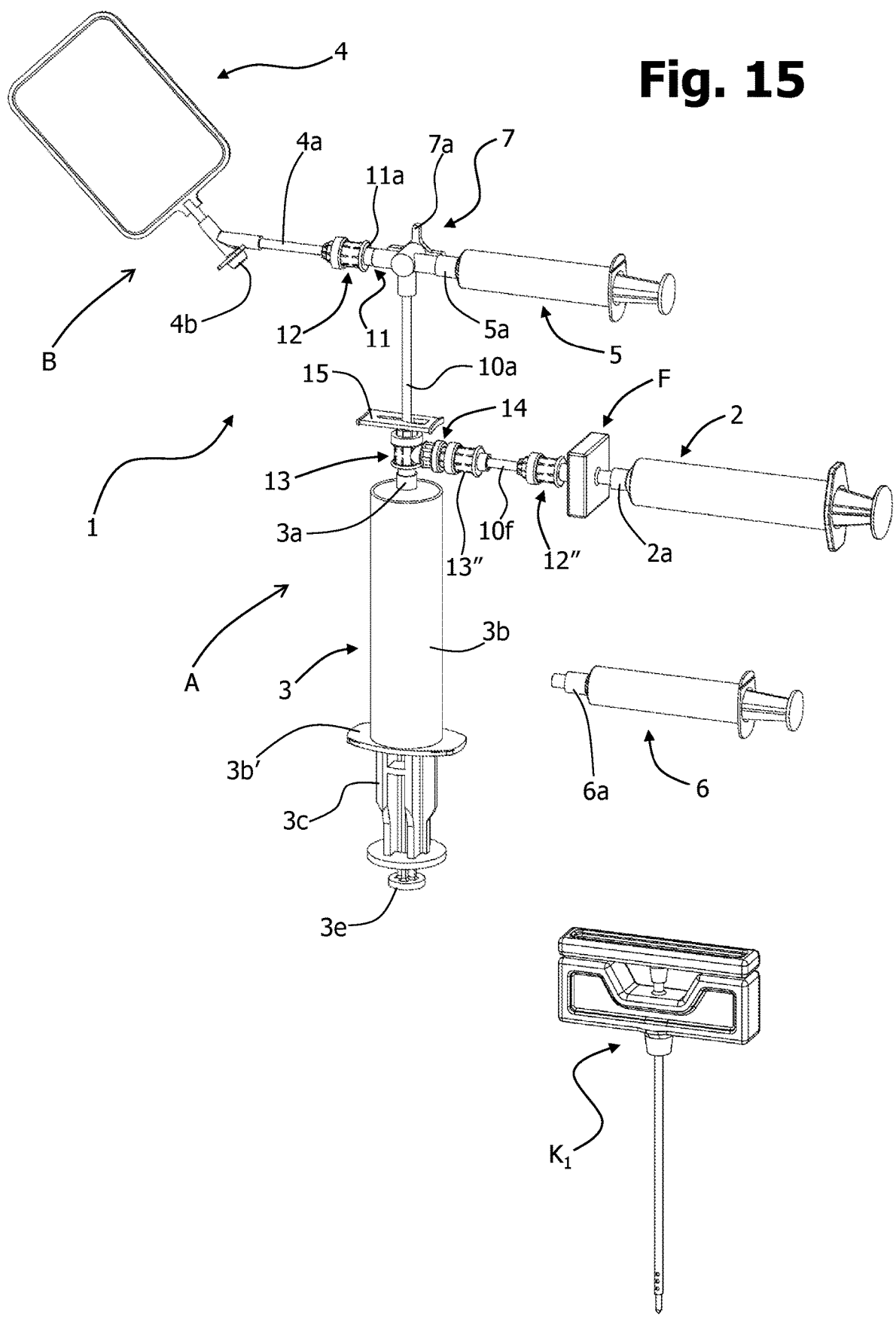
FIG. 15 is an exploded schematic view of a medical device according to a further embodiment to the invention.

FIG. 15 illustrates a variant embodiment, of preferred use for the case of a device 1 for treatment of medullary aspirate. In this figure, the same reference numbers as those of the previous figures are used to designate elements technically equivalent to the ones already described.

The device 1 of FIG. 15 differs from those of FIG. 1 basically for the presence of a filter F associated to the syringe 2, having the function of preventing passage towards the treatment container 3 of the particles of larger size that might be present in the medullary aspirate. The filter F may be relatively coarse, with passages for the fluid of dimensions indicatively comprised between 100 and 200 µm.

In the example illustrated, the filter has—on one side—an attachment that can be directly coupled to the attachment 2a of the syringe 2 and, on the other side, an attachment that can be coupled to a corresponding attachment of the device 1 or an attachment defined by the body of an automatic-closing or one-way valve 12", of a type similar to the valve 12. Preferentially, the outlet of the filter or of the valve 12" is connected to a flexible tube 10f, the opposite end of which is provided with an attachment 13" that can be separably coupled to the device 1, in particular to the attachment 14 of the connector 13.

The graphs of FIGS. 16-19 regard examples of detection of blood components in a buffy coat obtained from medullary aspirate with devices according to the invention, by carrying out a sampling every 2 ml. Following upon centrifugation, present in the buffy coat is also a considerable amount white blood cells (WBC) and a high dose of platelets, typically sedimented in a layer overlying the nucleated cells.

Figure 16:
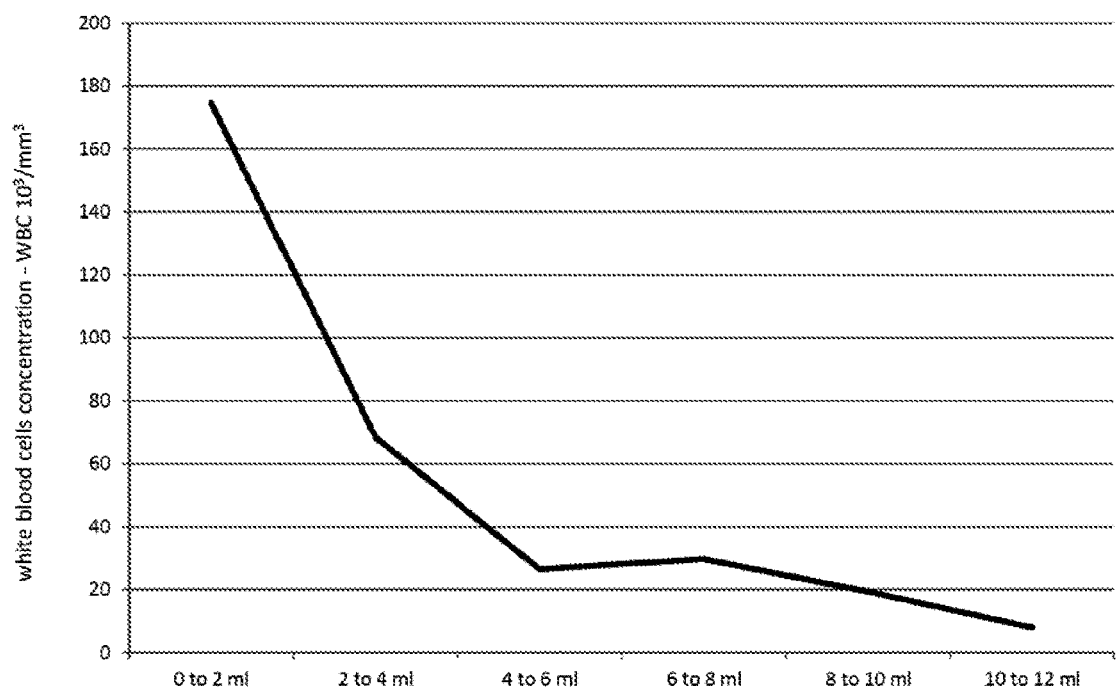
FIGS. 16-19 are graphs of examples of concentration of blood components obtained by sampling a buffy coat obtained using the procedure according to the invention.

The graph of FIG. 16 highlights the plot of the concentration of white blood cells and stromal or stem cells, measured by carrying out the aforesaid sampling every 2 ml: from the graph it emerges how the first portion of the buffy coat is richer in these cells. The concentration of leukocytes and stem cells drops following an exponential curve as deeper layers are sampled within the syringe 3.

Figure 17:
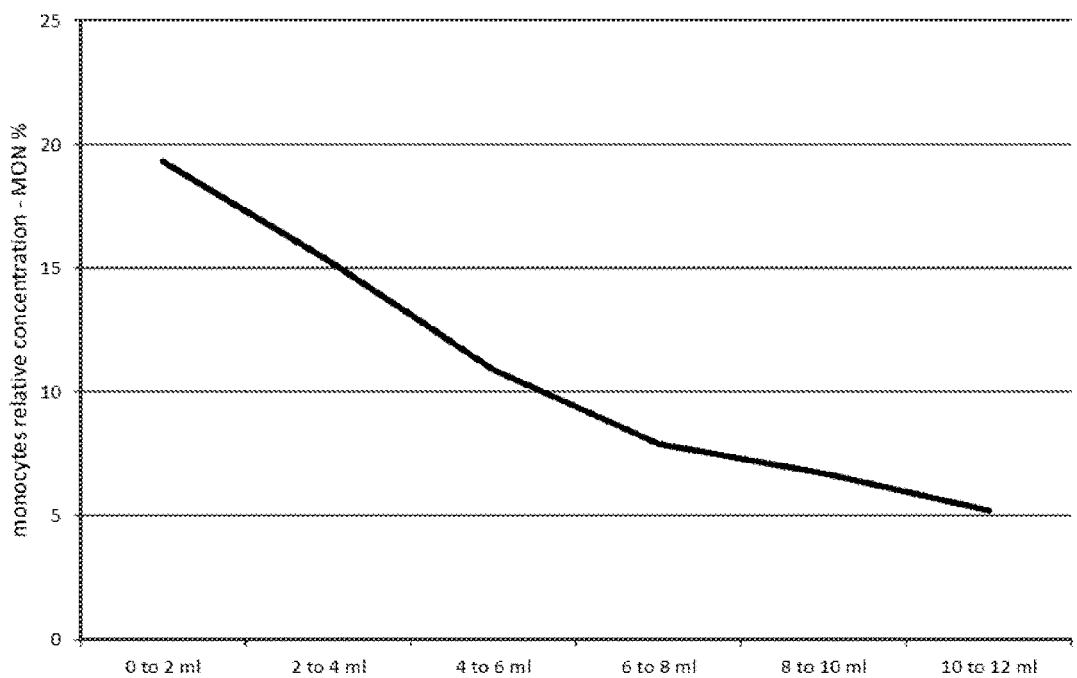

From the graph of FIG. 17 there may, instead, be noted the plot of the concentration of mononucleated cells (monocytes), within which the component of stem cells is present. Purely by way of example, and considering a sampling of 50 ml of blood plus 5 ml of anticoagulant, by sampling the first 8 ml of buffy coat, more than 95% of the mononucleated cells, and hence of the stem cells present therein, are collected.

Figure 18:
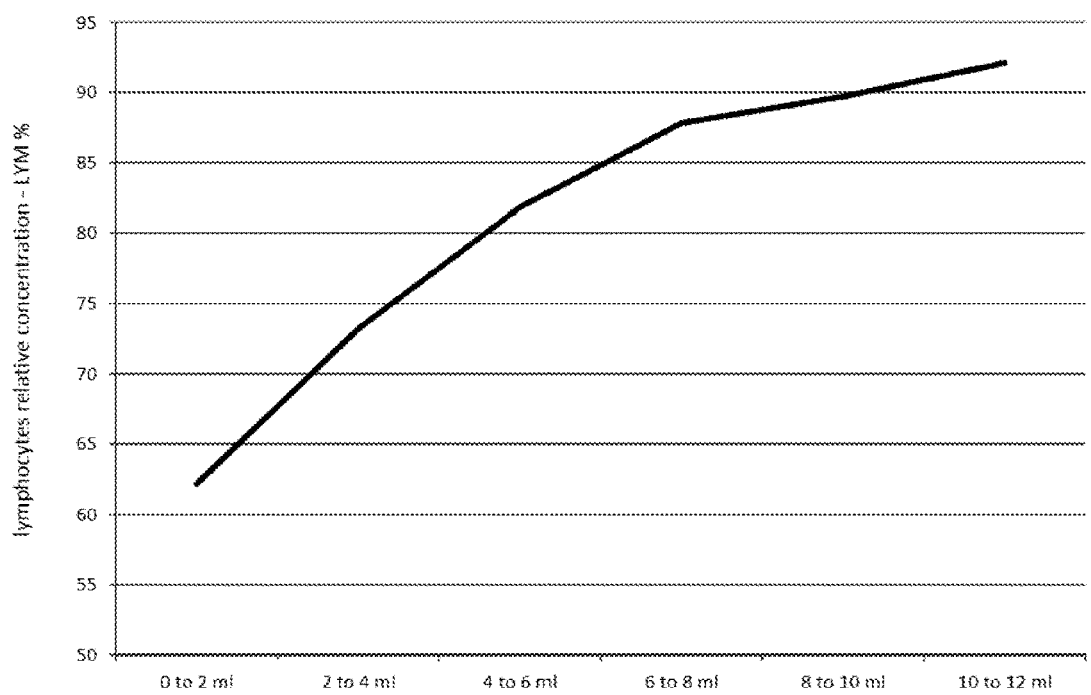
Figure 19:
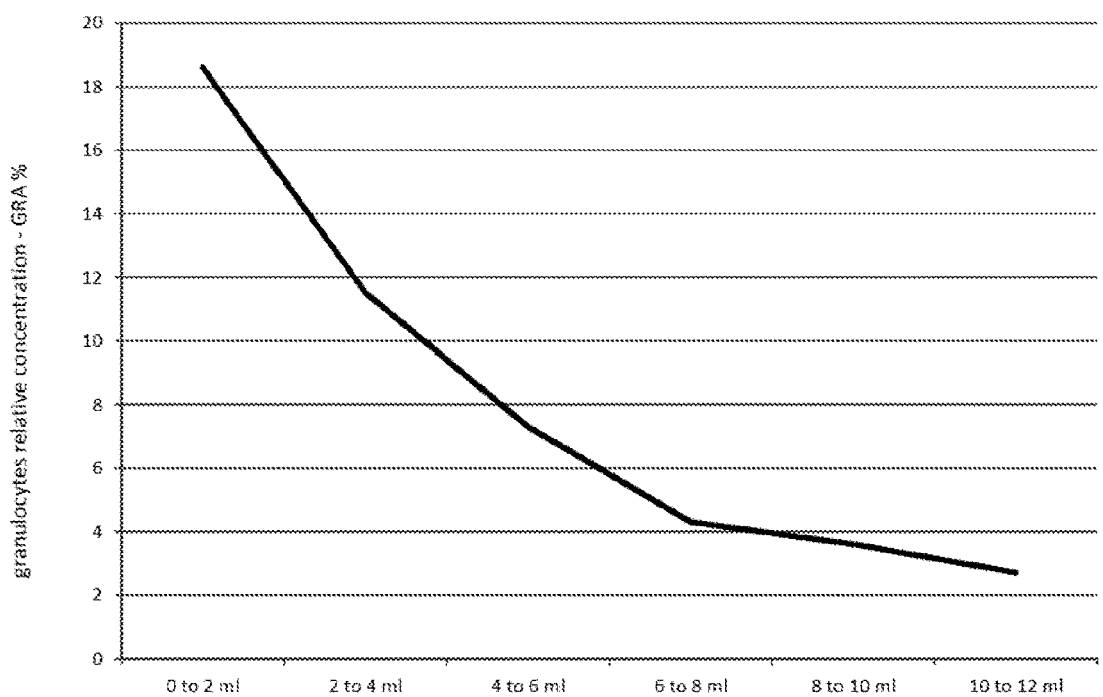

From the graph of FIG. 18, it may be noted that typically the relative percentage of lymphocytes rises as sampling of successive layers of buffy coat proceeds; however, also in the initial step lymphocytes constitute the largest fraction of leukocytes. This characteristic is particularly significant for the purposes of applications in which the concentration of monocytes is to be maximized maintaining in any case a high concentration of lymphocytes. From the graph of FIG. 19 it may be noted that the granulocytes follow an inverse plot, in the sense that their relative percentage drops as sampling of successive layers of buffy coat proceeds.

As may be appreciated, the system proposed enables effective separation of the buffy coat, and, according to the amount of material sampled, different cell populations can be obtained. The operator hence has the possibility of choosing the amount of buffy coat to be sampled also as a function of the desired components (leukocytes, monocytes, etc.). The operator is also afforded the possibility of diluting the sampled amount of buffy coat with plasma, by diverting immediately a part of the latter into the container 5 for collection of the buffy coat instead of into the corresponding bag 4, or else by subsequently sampling from the bag 4 into which it was previously conveyed.

From the foregoing description, the characteristics of the present invention emerge clearly, as likewise do its advantages, which are mainly represented by the simplicity of production of the disposable medical device proposed, by its contained cost, by its precision and simplicity of use and handling, and by its safety.

The modular makeup of the device is advantageous also in relation to the possibility of combining together modules having different characteristics, according to the requirements of use. The aforesaid modularity is particularly useful in the steps of production of the device, enabling production and storage of the various separate modules, which can be assembled on the basis of the customer's specifications. The modularity of the device avoids the need to store devices 1 in multiple complete configurations; i.e., it enables storage of the various separate modules, which can be assembled and packaged rapidly as required, preferably in sterile environment, with a reduction in the storage costs and a faster production and/or delivery to the customer. The modules A and/or B and/or C can be produced separately, assembled together to obtain a device 1, which is packaged and sterilized for subsequent use.

Also the methodologies of separation and concentration proposed, as well as the corresponding apparatus, are advantageous, as likewise its simplicity of implementation, effectiveness, and precision.

The system proposed enables effective separation of the buffy coat, affording the operator the choice of the amount of buffy coat to be sampled and the possibility, if need be, of diluting with plasma the desired amount of buffy coat.

Particularly advantageous is the possibility of separating the modules of the device without any risks of contamination of the fluid by the external environment, in particular thanks to the presence of means or valves for shut-off or automatic closing of the ducts, preferably set in the proximity or in the hydraulic connectors. The possibility of separation of the modules moreover enables a more convenient handling of the device during the steps of use thereof and its disposal.

The apparatus that can be used in the system proposed, which is also simple to produce and use, enables automation and guarantees precision of the operation of separation of the fractions of the venous blood or of the medullary aspirate.

It is clear that numerous variations may be made by the person skilled in the art to the device, the system, and the method described by way of example, without thereby departing from the scope of the invention as defined by the annexed claims.

The automatically operated valve or valves used in the device do not have to be necessarily integrated in respective attachments or connectors, but can be operatively arranged in the proximity of these connectors, on a corresponding branch of line or tube.

In a possible variant (not represented), the apparatus 60 is prearranged so as to operate the plunger stem of the syringe 3, instead of just its head 3d. In such an embodiment, hence, after the centrifugation carried out on the syringe 3, the latter must be again provided with the corresponding stem 3c, which is to be coupled to the corresponding head 3d. In this case, the actuation member previously designated by 63a of the apparatus 60 is replaced by a different element, designed to couple to the stem 3c in its part external to the barrel 3b. For this purpose, for example, the stem 3c may be provided with a transverse seat or cavity—such as the one partially visible in FIG. 2, reference 3f-preferably a through seat. In particular, the seat 3f is located in a proximal end region of the plunger stem, preferably in such a way that at least one part of the seat itself is located in a portion of the stem 3c that is always on the outside of the barrel 11. In such a variant, the apparatus 60 may possibly be prearranged for ensuring also recession of the plunger of the syringe 3, for example for the purposes of an automated sampling of the anticoagulant or of the medullary or venous blood, for instance in the case of use of the device 1".

It is also possible to configure the apparatus 60 so as to keep the plunger or the plunger head of the syringe 3 in a stationary position, moving instead the corresponding barrel 3b in an axial direction (for example, by rendering displaceable the part of the support 62 that integrates the seat 62a).

According to possible variant embodiments, at least some of the aforesaid operations, such as the operations of transfer of the plasma into the container 4 and of the concentrate of stromal cells into the container 5, can be carried out without the aid of the apparatus 60. In this case, after centrifugation of the treatment container 3, to the plunger head 3d of the latter there is again associated the corresponding stem 3c, with the latter and the valve 7 that are manually operated to obtain the aforesaid operations and/or the aforesaid transfer.

The invention claimed is:

1. A medical device for centrifugal separation of a concentrate enriched with cells from a biological fluid, in particular a concentrate of stromal or stem cells from medullar aspirate or venous blood, comprising:
   a treatment container, for receiving and treating the biological fluid for the purposes of its separation into a number of fractions;
   a first collection container, for receiving a first fraction of the fluid, in particular a fraction poor in said cells;
   a second collection container, for receiving a second concentrated fraction of the fluid enriched with said cells;
   a deviator valve having a first way connected or prearranged for connection to the treatment container, a second way connected or prearranged for connection to the first collection container, and a third way connected or prearranged for connection to the second collection container;
   a first connection line for connection of the treatment container to the first way of the deviator valve, a second connection line for connection of the first collection container to the second way of the deviator valve, and a third connection line for connection of the second collection container to the third way of the deviator valve,
   wherein the treatment container is a syringe container with a plunger having a plunger stem associated in a releasable way to a corresponding plunger head via a coupling arrangement, the plunger stem being releasable from the plunger head prior to centrifugation of the treatment container,
   wherein the first connection line comprises a first transparent tube, in particular a flexible transparent tube, and at least one of the second and third connection lines preferably comprises a second flexible tube; and
   wherein at least one connection line, or each connection line, further comprises:
      at least one respective hydraulic connector including two mutually coupling parts, for separable connection of a corresponding tube to the corresponding container and/or to the corresponding way of the deviator valve; and
      at least one self-closing valve.

2. The device according to claim 1, wherein at least one said self-closing valve defines, or comprises, or has integrated therein, at least one said coupling part of the at least one hydraulic connector.

3. The device according to claim 1, wherein the second way of the deviator valve comprises or has associated thereto a first coupling part of a first separable hydraulic connector, and said self-closing valve comprises or has associated thereto a second coupling part of the first hydraulic connector.

4. The device according to claim 1, wherein the third way of the deviator valve comprises or has associated thereto a hydraulic-connector part prearranged for separable direct coupling to a hydraulic-connector part of the second collection container.

5. The device according to claim 1, wherein:
   a first hydraulic connector of the first connection line is a connector with a number of attachments; and/or
   the tube of the first connection line has associated thereto, at an end thereof opposite to the first way of the deviator valve, a part of a hydraulic connector that can be separably coupled to an attachment of the treatment container.

6. The device according to claim 5, wherein the first hydraulic connector defines a first hydraulic-connector part, prearranged for direct coupling to a hydraulic-connector part of the treatment container, and a second hydraulic-connector part, prearranged for releasable connection to a fluid-sampling device comprising at least one of a device for sampling the biological fluid and a device for sampling an auxiliary substance, in particular an anticoagulant.

7. The device according to claim 1, further comprising at least one needle for sampling the biological fluid from a patient.

8. The device according to claim 1, wherein at least the treatment container, the first collection container, the second collection container, the deviator valve, and the connection lines with the associated at least one hydraulic connector and at least one self-closing valve are connected together and contained in a sterile package.

9. The device according to claim 1, wherein the at least one self-closing valve is configured to enable one-way flow in the respective connection line.

10. The device according to claim 1, wherein the at least one self-closing valve is configured to close automatically the respective connection line in case of separation of the two coupling parts of the at least one hydraulic connector.

11. A system for centrifugal separation of a concentrate enriched with cells from a biological fluid, in particular a concentrate of stromal or stem cells from medullar aspirate or venous blood, the system comprising at least a medical separation device according to claim 1.

12. The system according to claim 11, further comprising an apparatus that comprises:
    first actuation means, for causing in an automated way a relative displacement between a barrel of the treatment container of the medical separation device and at least one of the plunger stem and the plunger head of the treatment container of the medical separation device;
    second actuation means, for actuating in an automated way the deviator valve of the medical separation device;
    detection means, in particular of an optical or electromagnetic type, configured for detecting at least one characteristic of a flow passing in the first connection line connected to the treatment container of the medical separation device;
    a control system, prearranged for controlling in a coordinated way the first actuation means and the second actuation means according to detections made using the detection means, for the purposes of controlled delivery of a fraction poor in said cells of the biological fluid to the first collection container of the medical separation device and of controlled delivery of a fraction enriched with said cells in the second collection container of the medical separation device.

13. The system according to claim 12, wherein the apparatus further comprises at least one of:
    means for support and/or predefined positioning of the treatment container of the medical separation device with respect to the first actuation means, preferably configured for keeping the treatment container in a generally vertical position;
    means for support and/or predefined positioning of at least one stretch of the first connection line of the medical separation device with respect to the detection means;
    means for support and/or predefined positioning of the deviator valve of the medical separation device with respect to the second actuation means; and
    means for support and/or positioning of the second collection container of the medical separation device, preferably configured for keeping the second collection container in a substantially horizontal position.

14. The system according to claim 12, wherein the apparatus further comprises at least one of:
    sensor means for detecting the position of at least one movable member belonging to the first actuation means; and
    sensor means for detecting the position of at least one movable member belonging to the second actuation means.

15. A method for separating by centrifugation a concentrate enriched with cells from a biological fluid, in particular a concentrate of stromal or stem cells from medullar aspirate or venous blood, comprising the steps of:
    i) provding a medical separation device according to claim 1;
    ii) delivering to the treatment container a mixture comprising the biological fluid and an auxiliary substance, in particular an anticoagulant;
    iii) subjecting to centrifuging the mixture contained in the treatment container, in order to separate it or stratify it into at least one layer of sediment closer to the plunger head, an intermediate layer enriched in said cells, and a supernatant layer closer to a port or opening of the treatment container;
    iv) setting or keeping in fluid communication, via the deviator valve, the treatment container and the first collection container;
    v) transferring from the treatment container to the first collection container at least one first part of the supernatant layer, poor in cells, by starting a displacement of the plunger head;
    vi) setting in fluid communication, via the deviator valve, the treatment container and the second collection container; and
    vii) transferring from the treatment container to the second collection container the intermediate layer enriched with said cells, possibly in combination with a second part of the supernatant layer.

16. A medical system for centrifugal separation of a concentrate enriched with cells from a biological fluid, in particular a concentrate of stromal or stem cells from medullar aspirate or venous blood, comprising a medical separation device according to claim 1 and an apparatus that includes at least one of:
    actuation means, for causing in an automated way a displacement of at least one part of a container of the medical separation device;
    actuation means, for actuating in an automated way a deviator valve of the medical separation device;
    detection means, in particular of an optical or electromagnetic type, configured for detecting at least one characteristic of a biological fluid or of a corresponding fraction;
    means for support and/or predefined positioning of at least one container of the medical separation device;
    means for support and/or predefined positioning of at least one stretch of the first connection line of the medical separation device with respect to the detection means;
    means for support and/or predefined positioning of a deviator valve of the medical separation device;
    means for opening and closing a device for support and/or positioning of at least one part of the medical separation device;
    means for articulation of at least one element for opening and/or closing a device for support and/or positioning of at least one part of the medical separation device;
    sensor means for detecting the position of at least one movable member belonging to the actuation means.

* * * * *